(12) United States Patent
Murdock et al.

(10) Patent No.: US 10,578,614 B2
(45) Date of Patent: Mar. 3, 2020

(54) BAW SENSOR FLUIDIC DEVICE WITH INCREASED DYNAMIC MEASUREMENT RANGE

(71) Applicant: Qorvo US, Inc., Greensboro, NC (US)

(72) Inventors: Bruce Murdock, Bend, OR (US); Rio Rivas, Bend, OR (US)

(73) Assignee: QORVO BIOTECHNOLOGIES, LLC, Plymouth, MN (US)

( * ) Notice: Subject to any disclaimer, the term of this patent is extended or adjusted under 35 U.S.C. 154(b) by 226 days.

(21) Appl. No.: 15/453,433

(22) Filed: Mar. 8, 2017

(65) Prior Publication Data
US 2017/0261503 A1  Sep. 14, 2017

Related U.S. Application Data

(60) Provisional application No. 62/306,799, filed on Mar. 11, 2016.

(51) Int. Cl.
*G01N 33/543* (2006.01)
*G01N 29/02* (2006.01)
(Continued)

(52) U.S. Cl.
CPC ..... *G01N 33/54386* (2013.01); *G01N 29/022* (2013.01); *G01N 33/5438* (2013.01); *H01L 41/1132* (2013.01); *H01L 41/187* (2013.01); *H01L 41/22* (2013.01); *G01N 2291/02466* (2013.01)

(58) Field of Classification Search
CPC ......... G01N 33/54386; G01N 33/5438; G01N 29/022; G01N 29/222; H01L 41/22; H01L 41/187; H01L 41/1132; H03H 9/175
See application file for complete search history.

(56) References Cited

U.S. PATENT DOCUMENTS

| 4,640,756 A | 2/1987 | Wang et al. |
| 6,827,095 B2 | 12/2004 | O'Connor et al. |

(Continued)

FOREIGN PATENT DOCUMENTS

WO   WO 2017/075344 A1   5/2017

OTHER PUBLICATIONS

Nicu, Liviu et al., "Biosensors and tools for surface functionalization from the macroto the nanoscale: The way forward," Journal of Applied Physics, vol. 104, No. 11, Dec. 2008, pp. 111101-1 to 111101-16.

(Continued)

*Primary Examiner* — Melanie Brown
(74) *Attorney, Agent, or Firm* — Mueting, Raasch & Gebhardt, P.A.

(57) ABSTRACT

A fluidic device includes a base structure including at least one bulk acoustic wave (BAW) resonator structure having a fluidic passage containing at least one functionalized active region overlaid with functionalization material suitable to bind an analyte. One or more of a wall structure, a cover structure, or a portion of the base structure defining the fluidic passage includes additional functionalization material to form at least one absorber configured to bind at least one analyte. The dynamic measurement range of a BAW resonator structure is increased when the at least one absorber is placed upstream of the at least one functionalized active region.

20 Claims, 14 Drawing Sheets

(51) Int. Cl.
  *H01L 41/113* (2006.01)
  *H01L 41/187* (2006.01)
  *H01L 41/22* (2013.01)

(56) References Cited

U.S. PATENT DOCUMENTS

| | | | | |
|---|---|---|---|---|
| 6,955,787 | B1* | 10/2005 | Hanson | G01N 29/022 |
| | | | | 29/592 |
| 7,468,608 | B2 | 12/2008 | Feucht et al. | |
| 8,409,875 | B2 | 4/2013 | Johal et al. | |
| 2004/0086427 | A1* | 5/2004 | Childers | B01L 3/502707 |
| | | | | 422/400 |
| 2005/0148065 | A1 | 7/2005 | Zhang et al. | |
| 2006/0125487 | A1* | 6/2006 | Itomi | G01N 33/2888 |
| | | | | 324/533 |
| 2006/0133952 | A1* | 6/2006 | Zhang | B82Y 15/00 |
| | | | | 422/400 |
| 2006/0222568 | A1 | 10/2006 | Wang et al. | |
| 2009/0184002 | A1* | 7/2009 | Furukawa | G01N 33/5438 |
| | | | | 205/775 |
| 2011/0014719 | A1* | 1/2011 | Sijbers | B03C 1/282 |
| | | | | 436/150 |
| 2017/0110300 | A1 | 4/2017 | McCarron et al. | |

OTHER PUBLICATIONS

Pramanik, Sumit et al., "Developments of Immobilized Surface Modified Piezoelectric Crystal Biosensors for Advanced Applications," International Journal of Electrochemical Science, vol. 8, No. 6, Jan. 2013, pp. 8863-8892.

Qorvo US, Inc., "Summary of Sales Activity of Predecessor to Applicant Concerning Tilted C-Axis Aluminum Nitride Products," Unpublished, Jan. 10, 2017, 1 page.

Chen, Ying-Chung et al., "The Liquid Sensor Using Thin Film Bulk Acoustic Resonator with C-Axis Tilted AlN Films," Journal of Nanomaterials, vol. 2013, Article ID 245095, 2013, 8 pages.

Corso, Christopher et al., "Development of a Simple Inexpensive Bulk Acoustic Wave (BAW) Nanosensor for Cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.

Groner, M. D. et al., "Gas diffusion barriers on polymers using $Al_2O_3$ atomic layer deposition," Applied Physics Letters, vol. 88, Jan. 31, 2006, pp. 051907-1 to 051907-3.

Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré—Nancy I, Thesis, Sep. 14, 2006, 225 pages.

Meyer, Jens et al., "$Al_2O_3/ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.

Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.

Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.

Nirschl, Martin et al., "CMOS-Integrated Film Bulk Acoustic Resonators for Label-Free Biosensing," Sensors, vol. 10, No. 5, Apr. 27, 2010, pp. 4180-4193.

Yu, Hongyu et al., "Ultra Temperature-Stable Bulk-Acoustic-Wave Resonators with $SiO_2$ Compensation Layer," IEEE Transactions on Ultrasonics, Ferroelectrics, and Frequency Control, vol. 54, No. 10, Oct. 2007, pp. 2102-2109.

Zhou, Yan et al., "Interfacial Structures and Properties of Organic Materials for Biosensors: An Overview," Sensors, vol. 12, Nov. 6, 2012, pp. 15036-15062.

Gabl et al., "Novel Integrated FBAR Sensors: a Universal Technology Platform for Bio- and Gas-Detection," Proceedings of IEEE Sensors 2003. Abstract No. IEEE Cat. No. 03CH37498, IEEE International Conference on Sensors, Oct. 22, 2003 (*IEEE*) 2:1184.

International Patent Application No. PCT/US2017/021362, filed Mar. 8, 2017; [International Search Report / Written Opinion] dated May 30, 2017; 15 pages.

\* cited by examiner

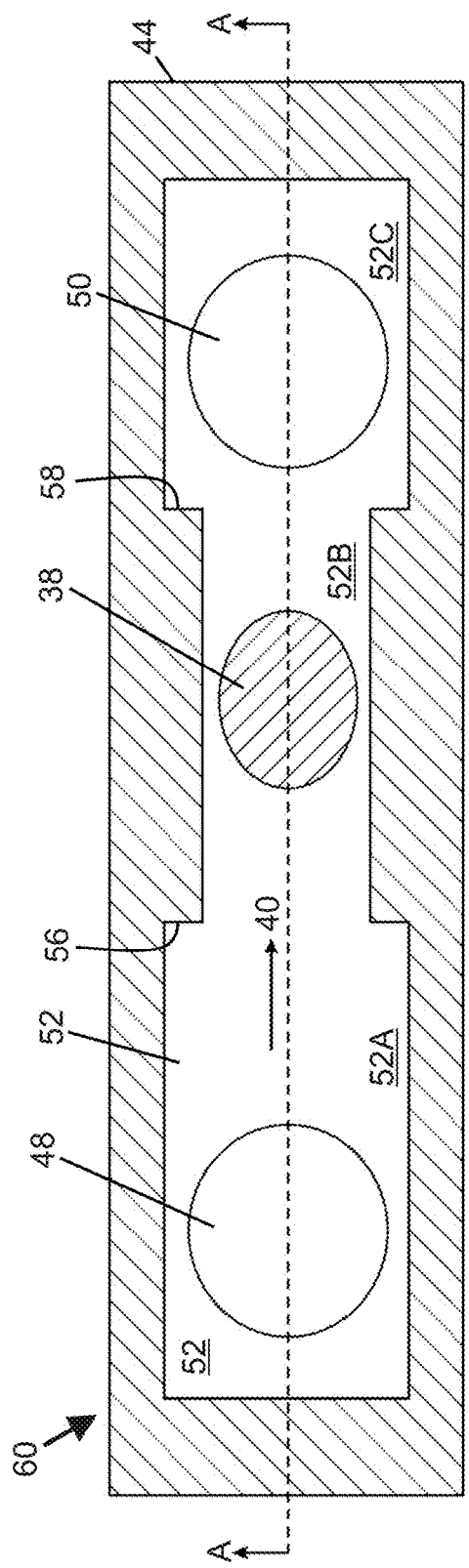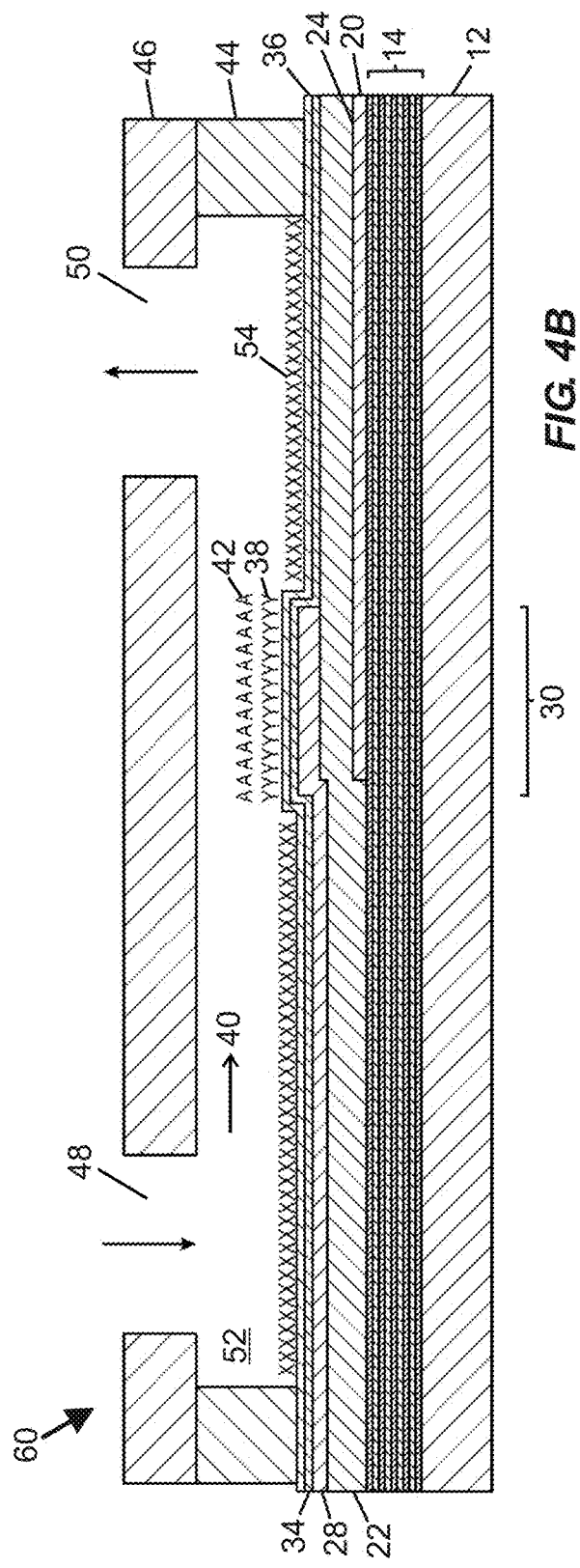

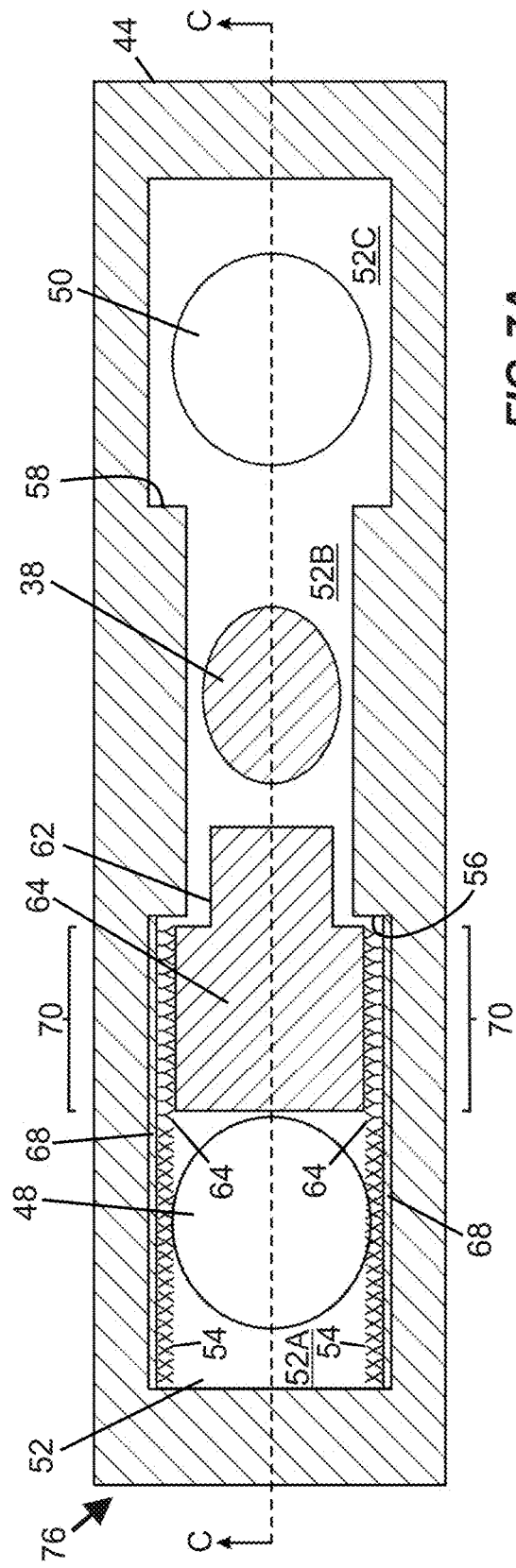
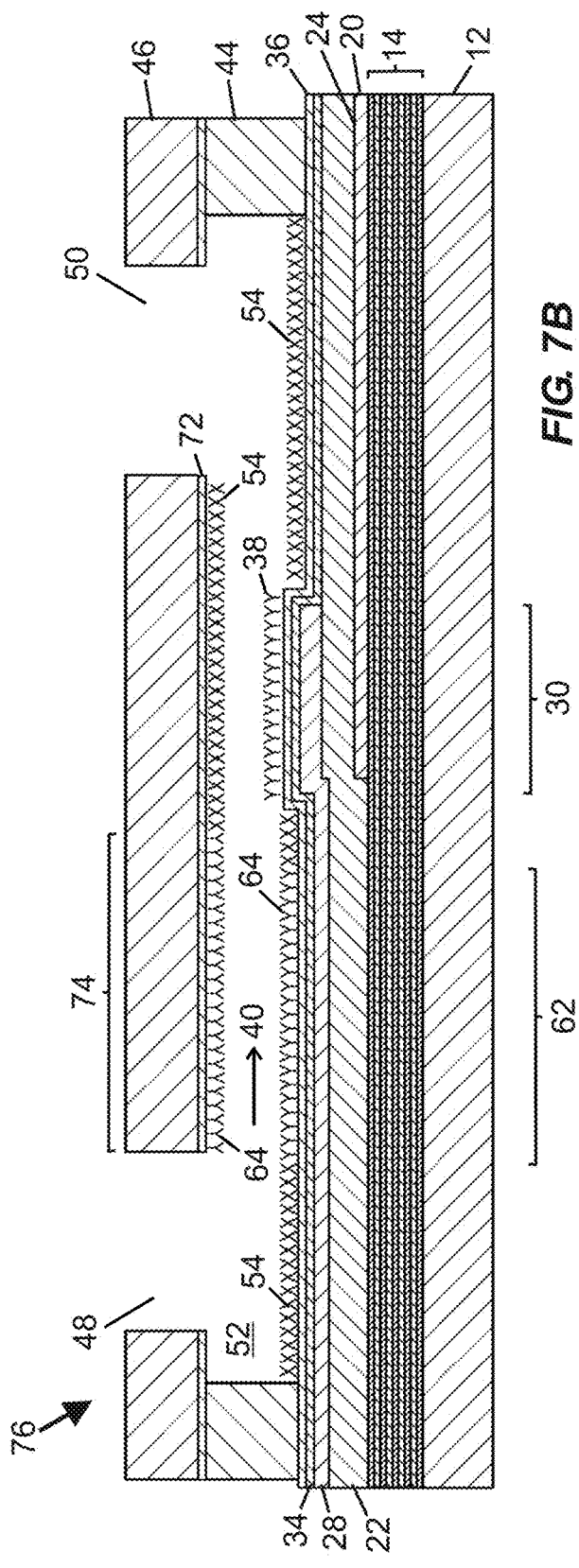
FIG. 7A
FIG. 7B

BAW SENSOR FLUIDIC DEVICE WITH INCREASED DYNAMIC MEASUREMENT RANGE

STATEMENT OF RELATED APPLICATIONS

This application claims the benefit of provisional patent application Ser. No. 62/306,799, filed Mar. 11, 2016, the disclosure of which is hereby incorporated by reference herein in its entirety.

TECHNICAL FIELD

The present disclosure relates to fluidic devices incorporating acoustic resonators, including fluidic devices and related systems suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a piezoelectric material, whereby any changes to the characteristics of the propagation path affect the velocity and/or amplitude of the wave. Presence of functionalization material embodied in a specific binding material along an active region of an acoustic wave device permits a specific analyte to be bound to the specific binding material, thereby altering the mass being vibrated by the acoustic wave and altering the wave propagation characteristics (e.g., velocity, thereby altering resonance frequency). Changes in velocity can be monitored by measuring the frequency, amplitude-magnitude, or phase characteristics of the acoustic wave device, and can be correlated to a physical quantity being measured.

In the case of a piezoelectric crystal resonator, an acoustic wave may embody either a bulk acoustic wave (BAW) propagating through the interior of a piezoelectric material, or a surface acoustic wave (SAW) propagating on the surface of the piezoelectric material. SAW devices involve transduction of acoustic waves (commonly including two-dimensional Rayleigh waves) utilizing interdigital transducers along the surface of a piezoelectric material, with the waves being confined to a penetration depth of about one wavelength. BAW devices typically involve transduction of an acoustic wave using electrodes arranged on opposing top and bottom surfaces of a piezoelectric material. In a BAW device, three wave modes can propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes, as the particle vibration, or polarization, is neither purely parallel nor purely perpendicular to the propagation direction. The propagation characteristics of the respective modes depend on the material properties and propagation direction respective to the c-axis orientations. The ability to create shear displacements is beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride (AlN) and zinc oxide (ZnO). To excite a wave including a shear mode using a piezoelectric material arranged between electrodes, a polarization axis in a piezoelectric thin film must generally be non-perpendicular to (e.g., tilted relative to) the film plane. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof.

Typically, BAW devices are fabricated by micro-electro-mechanical systems (MEMS) fabrication techniques owing to the need to provide microscale features suitable for facilitating high frequency operation. In the context of biosensors, functionalization materials (e.g., specific binding materials; also known as bioactive probes or agents) may be deposited on sensor surfaces by microarray spotting (also known as microarray printing) using a microarray spotting needle. Functionalization materials providing non-specific binding utility (e.g., permitting binding of multiple types or species of molecules) may also be used in certain contexts, such as chemical sensing.

Although the use of microscale active regions in BAW devices enables high frequency operation and provides high sensitivity, the limited amount of functionalization material that may be associated with an active region means that the functionalization material may be easily saturated—corresponding to a condition in which no binding sites of a functionalized active region are available to receive additional analyte. Once saturation occurs, measurement accuracy suffers, since analyte concentration cannot be accurately determined. Restated, a BAW device incorporating at least one functionalized microscale active region may suffer from limited dynamic measurement range, with the term "dynamic measurement range" representing a ratio between the largest and smallest measurement values that can be determined. Although it is possible to dilute samples to reduce the likelihood of saturation, the use of additional sample preparation equipment and steps increases the cost and complexity associated with sample analysis.

Thus, conventional biochemical sensing devices may suffer from limited dynamic measurement range, and may require cumbersome sample preparation (e.g., dilution) steps to avoid sensor saturation. Accordingly, there is a need for fluidic devices incorporating BAW resonator structures, such as for biosensing or biochemical sensing applications, that overcome limitations associated with conventional devices.

SUMMARY

The present disclosure relates to a fluidic device including a base structure, a wall structure, and a cover structure bounding a fluidic passage containing a functionalized active region of at least one bulk acoustic wave (BAW) resonator structure formed by the base structure, wherein one or more of the wall structure, the cover structure, or a portion of the base structure non-coincident with the functionalized active region comprises additional functionalization material to form at least one absorber (also referred to as "absorber region") configured to bind at least one analyte. The at least one absorber is configured to increase the dynamic measurement range of the fluidic device by reducing the likelihood of saturation of functionalization material of the functionalized active region of the at least one BAW resonator structure at a given analyte concentration. When multiple functionalized active regions are present, dynamic measurement range of a BAW resonator structure may be increased by interspersing absorbers in series with the functionalized active regions.

In one aspect, a fluidic device includes: a base structure comprising: (i) a substrate; (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region; and (iii) functionalization material arranged over at least a portion of the active region of the at least one bulk acoustic wave resonator structure to form at least one functionalized active region; a wall structure arranged over at least a portion of the base structure and defining lateral boundaries of a fluidic passage containing the active region and being configured to receive a fluid comprising multiple constituents; and a cover structure arranged over the wall structure and defining an upper boundary of the fluidic passage; wherein the base structure defines a lower boundary of the fluidic passage; and wherein one or more of the wall structure, the cover structure, or a portion of the base structure non-coincident with the active region comprises additional functionalization material to form at least one absorber configured to bind at least one analyte.

In certain embodiments, the at least one functionalized active region comprises a first aggregate surface area exposed to the fluidic passage, and the at least one absorber comprises a second aggregate surface area exposed to the fluidic passage that is greater than the first aggregate surface area exposed to the fluidic passage. In certain embodiments, the second aggregate surface area exposed to the fluidic passage is at least about 10 times greater than the first aggregate surface area exposed to the fluidic passage.

In certain embodiments, the additional functionalization material of the at least one absorber comprises a same chemical or biological composition as the functionalization material of the at least one functionalized active region.

In certain embodiments, the at least one bulk acoustic wave resonator structure comprises a plurality of bulk acoustic wave resonator structures; the at least one functionalized active region comprises a plurality of functionalized active regions; the at least one absorber comprises a plurality of absorbers; and at least some absorbers of the plurality of absorbers are arranged upstream of one or more functionalized active regions of the plurality of functionalized active regions, relative to a direction of flow of the fluid comprising multiple constituents through the fluidic passage.

In certain embodiments, the fluidic device further includes a blocking material arranged over at least a portion of one or more of the wall structure, the cover structure, or the base structure at locations non-coincident with the functionalization material or the additional functionalization material.

In certain embodiments, the wall structure and the cover structure are embodied in a monolithic body structure.

In certain embodiments, the wall structure and the base structure are embodied in a monolithic body structure.

In certain embodiments, the cover structure comprises a cover layer, the wall structure comprises at least one wall layer, and the at least one wall layer is arranged between the base structure and the cover layer.

In certain embodiments, the base structure further comprises at least one acoustic reflector element arranged between the substrate and the at least one bulk acoustic wave resonator structure.

In certain embodiments, the substrate defines a recess arranged below the active region.

In certain embodiments, the piezoelectric material comprises a c-axis having an orientation distribution that is predominantly non-parallel to normal of a face of the substrate.

In certain embodiments, the fluidic device further includes a self-assembled monolayer arranged between the functionalization material of the at least one functionalized active region and the top side electrode. In certain embodiments, the fluidic device further includes an interface layer arranged between the self-assembled monolayer and the top side electrode. In certain embodiments, the fluidic device further includes a hermeticity layer arranged between the interface layer and the top side electrode.

In certain embodiments, a method for biological or chemical sensing includes: supplying a fluid containing an analyte into the fluidic passage of the fluidic device as disclosed herein, wherein said supplying is configured to cause a first portion of the analyte to bind to the additional functionalization material of the at least one absorber and to cause a second portion of the analyte to bind to the functionalization material of the at least one functionalized active region; inducing a bulk acoustic wave in the active region of the at least one bulk acoustic wave resonator structure; and sensing a change in at least one of an amplitude-magnitude property, a frequency property, or a phase property of the at least one bulk acoustic wave resonator structure to indicate at least one of presence or quantity of analyte bound to the functionalization material of the at least one functionalized active region.

In another aspect, a method for fabricating a fluidic device includes: forming a base structure including at least one bulk acoustic wave resonator structure supported by a substrate, wherein the at least one bulk acoustic wave resonator structure includes a piezoelectric material, a top side electrode arranged over a portion of the piezoelectric material, a bottom side electrode arranged below at least a portion of the piezoelectric material, and an active region formed by a portion of the piezoelectric material arranged between the top side electrode and the bottom side electrode; forming a wall structure and a cover structure over at least a portion of the base structure, wherein: the wall structure defines lateral boundaries of a fluidic passage containing the active region and is configured to receive a fluid comprising multiple constituents, the cover structure is arranged over the wall structure and defines an upper boundary of the fluidic passage, and a lower boundary of the fluidic passage is defined by the base structure; depositing functionalization material over the active region of the at least one bulk acoustic wave resonator structure to form at least one functionalized active region; and depositing additional functionalization material over one or more of at least a portion of the wall structure, at least a portion of the cover structure, or a portion of the base structure non-coincident with the active region to form at least one absorber.

In certain embodiments, at least one of (i) depositing the functionalization material over the active region of the at least one bulk acoustic wave resonator structure, or (ii) depositing the additional functionalization material over one or more of at least a portion of the wall structure, at least a portion of the cover structure, or a portion of the base structure non-coincident with the active region, is performed after forming of at least one of the wall structure or the cover structure over at least a portion of the base structure.

In certain embodiments, the method further includes depositing a self-assembled monolayer over one or more of at least a portion of the wall structure, at least a portion of the cover structure, or a portion of the base structure non-coincident with the active region.

In certain embodiments, the method further includes depositing a blocking material over at least a portion of one or more of the wall structure, the cover structure, or the base structure at locations non-coincident with the functionalization material and non-coincident with the additional functionalization material.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure.

FIG. 4A is a schematic top plan view of the fluidic device portion of FIGS. 3A and 3B with a fluidic sample flowing within the fluidic passage over the functionalized active region.

FIG. 4B is a schematic cross-sectional view of the fluidic device portion of FIGS. 3A, 3B, and 4A, taken along section line A-A shown in FIG. 4A, with a fluidic sample flowing within the fluidic passage over the functionalized active region and with functionalization material overlying the functionalized active region being saturated with analyte bound thereto.

FIG. 7A is a schematic top plan view of a portion of a fluidic device including a fluidic passage bounded from below by a base structure incorporating a BAW resonator structure, bounded laterally by a wall structure, and bounded from above by a cover structure defining inlet and outlet ports, with a functionalized active region of the BAW resonator structure arranged generally between the inlet and outlet ports, and with absorber regions including additional functionalization material associated with the base structure, the wall structure, and the cover structure and arranged upstream of the functionalized active region, according to one embodiment of the present disclosure.

FIG. 7B is a schematic cross-sectional view of the fluidic device portion of FIG. 7A, taken along section line C-C shown in FIG. 7A, showing functionalization material associated with the functionalized active and absorber regions, and showing blocking material arranged over other portions of the base structure non-coincident with the functionalized active region and absorber regions, according to one embodiment.

DETAILED DESCRIPTION

Figure 1:
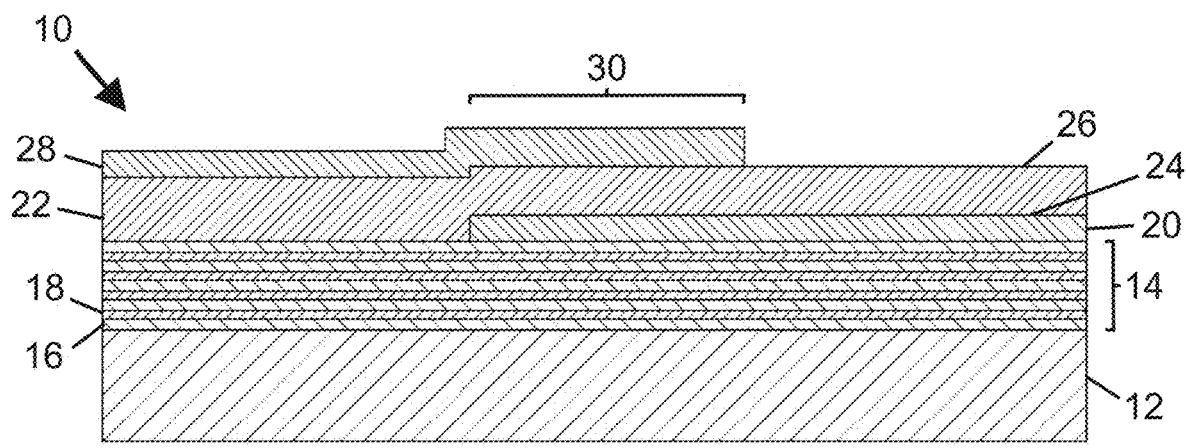
FIG. 1 is a schematic cross-sectional view of a portion of a bulk acoustic wave (BAW) MEMS resonator device usable with embodiments disclosed herein, including an active region with a piezoelectric material arranged between overlapping portions of a top side electrode and a bottom side electrode.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

The present disclosure relates to a fluidic device including a base structure, a wall structure, and a cover structure bounding a fluidic passage containing a functionalized active region of at least one bulk acoustic wave (BAW) resonator structure formed by the base structure. The fluidic passage is configured to receive a fluid including multiple constituents. One or more of the wall structure, the cover structure, or a portion of the base structure non-coincident with the functionalized active region comprises additional functionalization material to form at least one absorber configured to bind at least one analyte. The at least one absorber is configured to increase the dynamic measurement range of the fluidic device by reducing the likelihood of saturation of functionalization material of the functionalized active region of the at least one BAW resonator structure. Methods for fabricating a fluidic device as disclosed herein, as well as methods for biological or chemical sensing using such a fluidic device, are further provided.

Preferably, the at least one absorber is arranged upstream of the at least one BAW resonator structure, so that the at least one absorber can bind analyte in a flow of fluid before the fluid reaches a downstream functionalized active region. In certain embodiments, multiple BAW resonator structures including multiple functionalized active regions may be provided, and multiple absorber regions may be provided, wherein at least some absorber regions are arranged upstream of one or more active functionalized regions, relative to a direction of flow of through a fluidic passage containing the functionalized active regions and absorber regions. In certain embodiments, functionalized active regions and absorber regions including functionalization material may be arranged in sequence within a fluidic passage, with alternating placement of absorber regions and functionalized active regions.

In certain embodiments, a quantity of functionalization material of one or more absorber regions exceeds a quantity of functionalization material of one or more functionalized active regions. For example, at least one functionalized active region may include a first aggregate surface area exposed to the fluidic passage, and at least one absorber region may include a second aggregate surface area exposed to a fluidic passage that is greater than the first aggregate surface area exposed to the fluidic passage. In certain embodiments, a ratio of functionalization material of one or more absorber regions to functionalization material of one or more functionalized active regions (whether on the basis of mass, area, or number of binding sites) may be at least 1:1, at least 5:1, at least 10:1, at least 50:1, at least 100:1, at least 500:1, at least 1,000:1, at least 5,000:1, or at least 10,000:1, wherein the preceding open-ended ranges (where appropriate) may be optionally bounded by upper boundary ratios of up to 100:1, up to 500:1, up to 1,000:1, up to 5,000:1, up to 10,000:1, or up to 15:000:1.

In certain embodiments, functionalization material of the at least one absorber region may comprise the same chemical or biological composition as functionalization material of at least one functionalized active region, to enable the at least one absorber region to bind the same genus(es) and/or species of analyte as the at least one functionalized active region. In other embodiments, functionalization material of the at least one absorber region may comprise different chemical or biological composition than functionalization material of at least one functionalized active region, such as may be useful to remove species that compete with the species of interest, thereby also serving to increase dynamic range. In certain embodiments, the at least one absorber region and the at least one functionalized active region are functionalized with specific binding material. In other embodiments, the at least one absorber region and the at least one functionalized active region are functionalized with non-specific binding material.

In certain embodiments, a blocking material may be arranged over one or more surfaces bounding a fluidic passage at areas that are non-coincident with the functionalization material. Presence of a blocking material may prevent attachment of functionalization material and/or non-specific binding of analyte to an underlying self-assembled monolayer (SAM).

In certain embodiments, a BAW resonator structure comprises a hexagonal crystal structure piezoelectric material (e.g., aluminum nitride or zinc oxide) that includes a c-axis having an orientation distribution that is non-parallel (and also non-perpendicular) to normal of a face of a substrate over which the piezoelectric material is formed, thereby providing a quasi-shear mode acoustic resonator. Such a c-axis orientation distribution enables creation of shear displacements at certain frequencies (which beneficially enables operation of a BAW resonator-based sensing device in liquid environments), and enables creation of longitudinal displacements at other frequencies (which may be useful to promote localized mixing). Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric material having an inclined c-axis orientation are disclosed in U.S. Pat. No. 4,640,756 issued on Feb. 3, 1987, with the foregoing patent hereby being incorporated by reference herein.

Before describing fluidic devices with functionalized active regions and absorber regions including functionalization material, exemplary bulk acoustic wave MEMS resonator devices, associated layers useful for providing biochemical sensing utility, and fluidic devices incorporating MEMS resonator devices will be introduced.

Micro-electrical-mechanical system (MEMS) resonator devices according to certain embodiments include a substrate, a BAW resonator structure arranged over at least a portion of the substrate, and a functionalization material arranged over at least a portion of an active region of the BAW resonator structure. Various layers may be arranged between the functionalization material and a top side electrode (which is coincident with the active region of the BAW resonator structure), such as: a hermeticity layer (e.g., to protect a top side electrode from corrosion in a liquid environment), an interface layer, and/or a self-assembled monolayer (SAM), with the interface layer and/or the SAM being useful to facilitate attachment of at least one overlying material layer, ultimately including functionalization material. In certain embodiments, the interface layer facilitates attachment of an overlying SAM, and the SAM facilitates attachment of an overlying functionalization material. In certain embodiments, multiple functionalization materials may be provided.

FIG. 1 is a schematic cross-sectional view of a portion of a bulk acoustic wave (BAW) MEMS resonator device 10 useable with embodiments disclosed herein. The resonator device 10 includes a substrate 12 (e.g., typically silicon or another semiconductor material), an acoustic reflector 14 arranged over the substrate 12, a piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered an active region 30 of the resonator device 10. The acoustic reflector 14 serves to reflect acoustic waves and therefore reduce or avoid their dissipation in the substrate 12. In certain embodiments, the acoustic reflector 14 includes alternating thin layers 16, 18 of materials (e.g., silicon oxicarbide [SiOC], silicon nitride [$Si_3N_4$], silicon dioxide [$SiO_2$], aluminum nitride [AlN], tungsten

[W], and molybdenum [Mo]) having different acoustic impedance values, optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28.

In certain embodiments, the piezoelectric material 22 comprises a hexagonal crystal structure piezoelectric material (e.g., aluminum nitride or zinc oxide) that includes a c-axis having an orientation distribution that is predominantly non-parallel to (and may also be non-perpendicular to) normal of a face of the substrate 12. Under appropriate conditions, presence of a c-axis having an orientation distribution that is predominantly non-parallel to normal of a face of a substrate enables a BAW resonator structure to be configured to exhibit a dominant shear response upon application of an alternating current signal across a top side electrode and a bottom side electrode.

The bulk acoustic wave MEMS resonator device 10 shown in FIG. 1 lacks any layers (e.g., including functionalization material) overlying the active region 30 that would permit the resonator device 10 to be used as a biochemical sensor. If desired, at least portions of the resonator device 10 shown in FIG. 1 (e.g., including the active region 30) may be overlaid with various layers, such as one or more of: a hermeticity layer, an interface layer, a self-assembled monolayer (SAM), and/or a functionalization material (which may include specific binding material or non-specific binding material).

Figure 2:
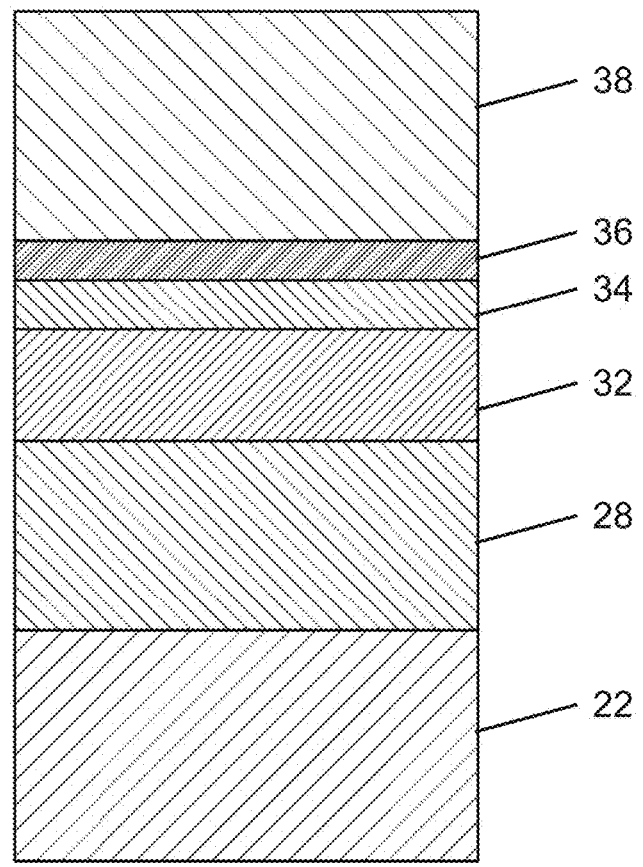
FIG. 2 is a schematic cross-sectional view of an upper portion of a BAW MEMS resonator device including a piezoelectric material and a top side electrode overlaid with a hermeticity layer, an interface layer, a self-assembled monolayer, and a functionalization (e.g., specific binding) material.

FIG. 2 is a schematic cross-sectional view of an upper portion of a BAW MEMS resonator device including a piezoelectric material 22 and a top side electrode 28 overlaid with a hermeticity layer 32, an interface layer 34, a self-assembled monolayer (SAM) 36, and a functionalization (e.g., specific binding) material 38. In certain embodiments, one or more blocking materials (not shown) may be applied during fabrication, such as over portions of the interface layer 34 to prevent localized attachment of one or more subsequently deposited layers, or (if applied over selected regions of the SAM 36 or functionalization material 38) to prevent analyte capture in regions not overlying the active region 30 of the BAW MEMS resonator device.

In certain embodiments, photolithography may be used to promote patterning of interface material or blocking material over portions of a MEMS resonator device. Photolithography involves use of light to transfer a geometric pattern from a photomask to a light-sensitive chemical photoresist on a substrate and is a process well known to those of ordinary skill in the semiconductor fabrication art. Typical steps employed in photolithography include wafer cleaning, photoresist application (involving either positive or negative photoresist), mask alignment, and exposure and development. After features are defined in photoresist on a desired surface, an interface layer may be patterned by etching in one or more gaps in a photoresist layer, and the photoresist layer may be subsequently removed (e.g., by using a liquid photoresist stripper, by ashing via application of an oxygen-containing plasma, or another removal process).

In certain embodiments, an interface layer (e.g., arrangeable between a top side electrode and a SAM) includes a hydroxylated oxide surface suitable for formation of an organosilane SAM. A preferred interface layer material including a hydroxylated oxide surface is silicon dioxide [$SiO_2$]. Alternative materials incorporating hydroxylated oxide surfaces for forming interface layers include titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer (e.g., arrangeable between a top side electrode and a SAM), or at least one electrode that is devoid of an overlying interface layer, includes gold or another noble metal (e.g., ruthenium, rhodium, palladium, osmium, iridium, platinum, or silver) suitable for receiving a thiol-based SAM that may be overlaid with functionalization material.

In certain embodiments incorporating electrode materials subject to corrosion, a hermeticity layer may be applied between a top side electrode and an interface layer. A hermeticity layer may be unnecessary when noble metals (e.g., gold, platinum, etc.) are used for top side electrodes. If provided, a hermeticity layer preferably includes a dielectric material with a low water vapor transmission rate (e.g., no greater than 0.1 $g/m^2/day$). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

In certain embodiments, a hermeticity layer and/or an interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer) due to its ability to provide excellent conformal coating with good step coverage over device features so as to provide layer structures that are free of pinholes. Moreover, ALD is capable of forming uniformly thin layers that provide relatively little damping of acoustic vibrations that would otherwise result in degraded device performance. Adequacy of coverage is important for a hermeticity layer (if present) to avoid corrosion of the underlying electrode. If ALD is used for deposition of a hermeticity layer, then in certain embodiments a hermeticity layer may include a thickness in a range of from about 10 nm to about 25 nm. In certain embodiments, hermeticity layer thickness is about 15 nm, or from about 12 nm to about 18 nm. Conversely, if another process such as chemical vapor deposition is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments. In certain embodiments, a hermeticity layer and an interface layer may be sequentially applied in a vacuum environment, thereby promoting a high-quality interface between the two layers.

If provided, a hermeticity layer may include an oxide, a nitride, or an oxynitride material serving as a dielectric material and having a low water vapor transmission rate (e.g., no greater than 0.1 g/m$^2$/day) according to certain embodiments. In certain embodiments, a hermeticity layer includes at least one of aluminum oxide [$Al_2O_3$] or silicon nitride [SiN]. In certain embodiments, an interface layer includes at least one of $SiO_2$, $TiO_2$, or $Ta_2O_5$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in BAW resonator structures, various transition and post-transition metals can be used for such electrodes.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group and are therefore useful for coupling inorganic materials to organic polymers. An organosilane SAM may be formed by exposing a hydroxylated oxide surface to an organosilane material in the presence of trace amounts of water to form intermediate silanol groups. These groups then react with free hydroxyl groups on the hydroxylated oxide surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more. Preferably, a SAM readily binds to the locally patterned interface layer but does not readily bind to other adjacent material layers (e.g., a hermeticity layer, a piezoelectric material, and/or a blocking material layer).

When an electrode and/or interface layer comprising gold or another noble metal is used, then thiol-based (e.g., alkanethiol-based) SAMs may be used. Alkanethiols are molecules with an S—H head group, a tail group, and a backbone comprising an alkyl chain. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, the SAM may be biologically functionalized, such as by receiving a functionalization (e.g., specific binding) material. In certain embodiments, specific binding materials may be applied on or over a SAM using a microarray spotting needle or other suitable methods. In certain embodiments, an interface layer may be patterned (e.g., using photolithographic masking and selective etching for defining the interface layer) with a high dimensional tolerance over only a portion of a BAW resonator structure (which includes a substrate), a SAM may be applied over the interface layer, and a subsequently applied specific binding material may be attached only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different specific binding materials may be provided over different active regions of a multi-resonator structure (i.e., one or more resonator structures including multiple active regions), optionally in combination with one or more active regions that are devoid of specific binding materials to serve as comparison (or "reference") regions. In certain embodiments, a functionalization (e.g., bio-functionalization) material may provide non-specific binding utility.

Certain embodiments are directed to a fluidic device including multiple bulk acoustic wave (BAW) MEMS resonator structures as disclosed herein and including a fluidic passage (e.g., a channel, a chamber, or the like) arranged to conduct a liquid to contact a functionalization (e.g., specific binding) material arranged over at least one active region of the BAW MEMS resonator structures. Such a device may be microfluidic in scale, and may comprise at least one microfluidic passage (e.g., having at least one dimension, such as height and/or width, of no greater than about 500 microns, or about 250 microns, or about 100 microns). For example, following fabrication of bulk acoustic wave MEMS resonator structures and deposition of a SAM over portions thereof (optionally preceded by deposition of a hermeticity layer and an interface layer), a microfluidic device may be fabricated by forming one or more walls defining lateral boundaries of a microfluidic passage over a first bulk acoustic wave MEMS resonator structure with an active region thereof arranged along a bottom surface of the microfluidic passage, and then enclosing the microfluidic passage using a cover or cap layer that may define fluidic ports (e.g., openings) enabling fluid communication with the microfluidic passage. In certain embodiments, functionalization (e.g., specific binding) material may be pre-applied to the active region of a bulk acoustic wave MEMS resonator structure before formation of the microfluidic passage; in other embodiments, functionalization material may be applied over an active region of a bulk acoustic wave resonator structure following formation of the microfluidic passage.

Walls of a microfluidic passage may be formed of any suitable material, such as laser-cut "stencil" layers of thin polymeric materials and/or laminates, optionally including one or more self-adhesive surfaces (e.g., adhesive tape). Optionally such walls may be formed prior to deposition of a SAM, functionalization material, and/or blocking layers, with an SU-8 negative epoxy resist or other photoresist material. In certain embodiments, a cover or cap layer may be integrally formed with one or more walls (e.g., via molding or another suitable process) to define a portion of an upper boundary as well as lateral boundaries of at least one fluidic passage, and the integrally formed partial cover/wall structure may be applied (e.g., adhered or otherwise bonded) over at least a portion of a bulk acoustic wave resonator structure to enclose the at least one fluidic passage.

In certain embodiments, a chemical or biological blocking material may be applied over a portion of a SAM to prevent attachment of a functionalization (e.g., specific binding) material over one or more selected regions of a BAW resonator structure (e.g., one or more regions apart from an active region). The proper choice of a chemical or biological blocking material (e.g., blocking buffer) for a given analysis depends on the type of target species or analyte present in a sample. Various types of blocking buffers such as highly purified proteins, serum, or milk may be used to block free sites on a SAM. Additional blockers include ethanolamine or polyethylene oxide (PEO)-containing materials. An ideal blocking buffer would bind to all potential sites of non-specific interaction away from an active region. To optimize a blocking buffer for a particular analysis, empirical testing may be used to determine signal-to-noise ratio. No single chemical or biological blocking material is ideal for every situation, since each antibody-antigen pair has unique characteristics.

Figure 3A:
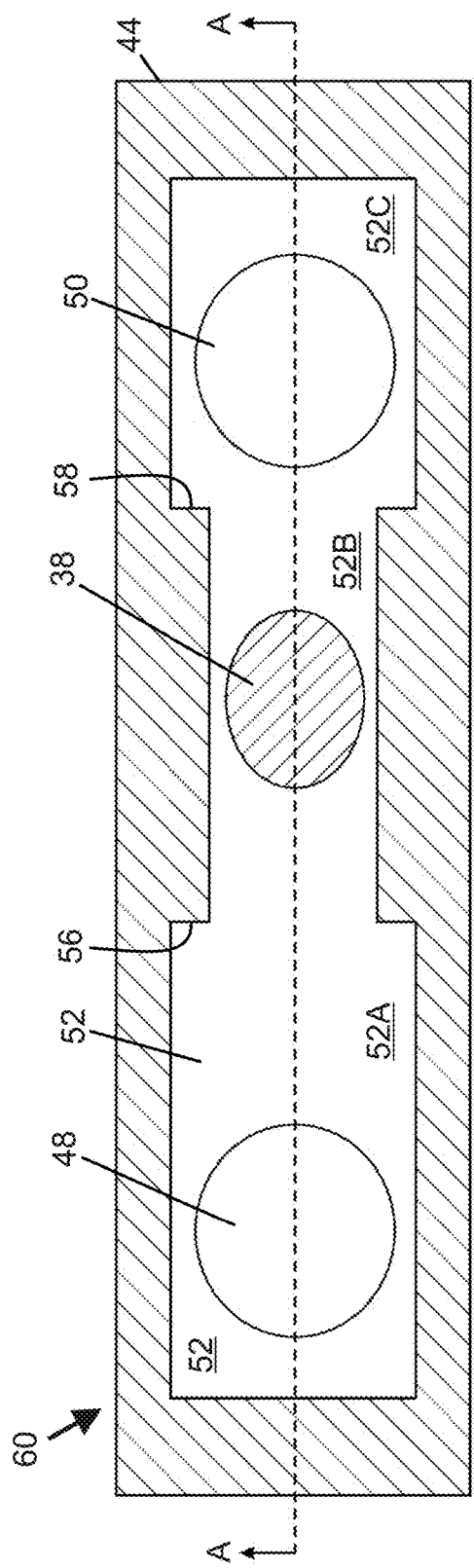
FIG. 3A is a schematic top plan view of a portion of a fluidic device including a fluidic passage bounded from below by a base structure incorporating a BAW resonator structure, bounded laterally by a wall structure, and bounded from above by a cover structure defining inlet and outlet ports, with a functionalized active region of the BAW resonator structure arranged generally between the inlet and outlet ports.
Figure 3B:
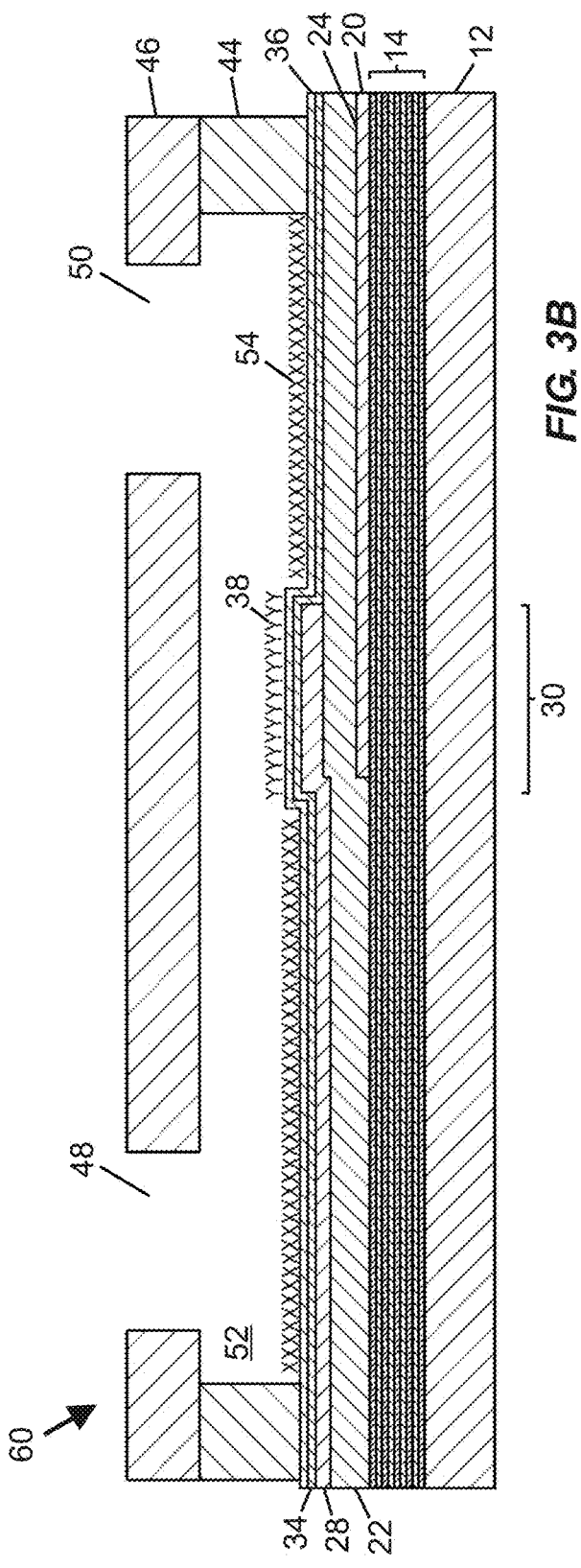
FIG. 3B is a schematic cross-sectional view of the fluidic device portion of FIG. 3A, taken along section line A-A shown in FIG. 3A, showing functionalization material arranged over the functionalized active region and showing blocking material arranged over other portions of the base structure non-coincident with the functionalized active region.

FIG. 3A provides a schematic top plan view, and FIG. 3B provides a schematic cross-sectional view, of at least a portion of a fluidic device 60 (e.g., a biochemical sensor device) devoid of any absorber region, embodying a first comparison device intended to provide context for subsequently described embodiments of the disclosure. The fluidic device 60 includes a fluidic passage 52 composed of an upstream segment 52A, a narrowed width intermediate segment 52B, and a downstream segment 52C. The fluidic passage 52 is bounded from below by a bulk acoustic wave (BAW) resonator structure including an active region 30, bounded laterally by a wall structure 44, and bounded from above by a cover structure 46 (which may be embodied in a cover or cap layer) defining a first fluidic port 48 (e.g., fluidic inlet port) and a second fluidic port 50 (e.g., fluidic outlet port). The intermediate segment 52B of the fluidic passage 52 contains the active region 30. First and second shoulder regions 56, 58 are arranged upstream and downstream, respectively, of inwardly projecting sidewall portions and define transitions (i) between the upstream segment 52A and the intermediate segment 52B, and (ii) between the intermediate segment 52B and the downstream segment 52C, respectively.

The fluidic device 60 includes a substrate 12 overlaid with an acoustic reflector 14, and a bottom side electrode 20 arranged generally below a piezoelectric material 22. A top side electrode 28 extends over a portion of the piezoelectric material 22, wherein a portion of the piezoelectric material 22 arranged between the top side electrode 28 and the bottom side electrode 20 embodies the active region 30 of the BAW resonator structure. The bottom side electrode 20 is arranged along a portion of a lower surface 24 of the piezoelectric material 22. The top side electrode 28 and the piezoelectric material 22 are overlaid with an interface layer 34 and a self-assembled monolayer (SAM) 36. In certain embodiments, a hermeticity layer (not shown) may be arranged under the interface layer 34. Portions of the SAM 36 non-coincident with the active region 30 (e.g., laterally arranged between the active region 30 and the wall structure 44) are overlaid with a chemical or biological blocking material 54 to prevent localized attachment of functionalization material and/or analyte. A portion of the SAM 36 that is registered with the active region 30 is overlaid with a layer of functionalization (e.g., specific binding) material 38 arranged to bind at least one analyte, to create a functionalized active region. The active region 30 is arranged proximate to (i.e., below) the fluidic passage 52 at a location between the first fluidic port 48 and the second fluidic port 50. The size of the active region 30 is dictated at least in part by an intended operating frequency of the corresponding BAW resonator structure. Although the active region 30 is shown as having a predominantly oval shape oriented with a long dimension parallel to the intended direction of flow within the fluidic passage 52, it is to be recognized that in certain embodiments, the active region 30 may be provided in any suitable shape and/or orientation, such as a round shape or an oval shape with a long dimension transverse to the intended direction of flow of fluid within the fluidic passage 52.

Walls of the wall structure 44 are laterally displaced from the active region 30 and extend upward from the SAM 36 to define lateral boundaries of the fluidic passage 52. The wall structure 44 may be formed of any suitable material, such as a laser-cut "stencil" layer of thin polymeric materials and/or laminate materials, optionally including one or more self-adhesive surfaces (e.g. adhesive tape). Optionally the wall structure 44 may be formed prior to deposition of the SAM 36, functionalization material 38, and chemical or biological blocking material 54 with an SU-8 negative epoxy resist or other photoresist material. The cover structure 46 serves as an upper boundary for the fluidic passage 52. The cover structure 46 may be formed by defining first and second fluidic ports 48, 50 (e.g., via laser cutting or water jet cutting) in a layer of an appropriate material (e.g., a substantially inert polymer, glass, silicon, ceramic, or the like), and adhering the cover structure 46 to top surfaces of the wall structure 44.

FIG. 4A provides a schematic top plan view, and FIG. 4B provides a schematic cross-sectional view, of the at least a portion of a fluidic device 60 of FIGS. 3A and 3B in operation. A fluid volume 40 (e.g., a fluid sample) is supplied through the first fluidic port 48 into the upstream segment 52A of the fluidic passage 52, then flowed through the intermediate segment 52B over the active region 30, and then flowed through the downstream segment 52C to the second fluidic port 50 to exit the fluidic passage 52. As shown in FIG. 4B, analyte 42 in the fluid volume 40 is bound to the functionalization material 38 overlying the active region 30 to the point that the functionalization material 38 is saturated (i.e., all binding sites of the functionalization material 38 are occupied with analyte 42). When a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte 42 bound to the functionalization material 38. Due to the saturation condition, however, the electroacoustic response of the BAW resonator structure may not accurately reflect the true concentration of analyte 42 in the fluid volume 40, since the fluidic device 60 lacks sufficient dynamic measurement range to detect a greater analyte concentration.

Having described the fluidic device 60 of FIGS. 3A-4B to provide context, fluidic devices including one or more functionalized absorbers configured to interact with fluid flowing within a fluidic passage to increase dynamic measurement range will now be described.

Figure 5A:
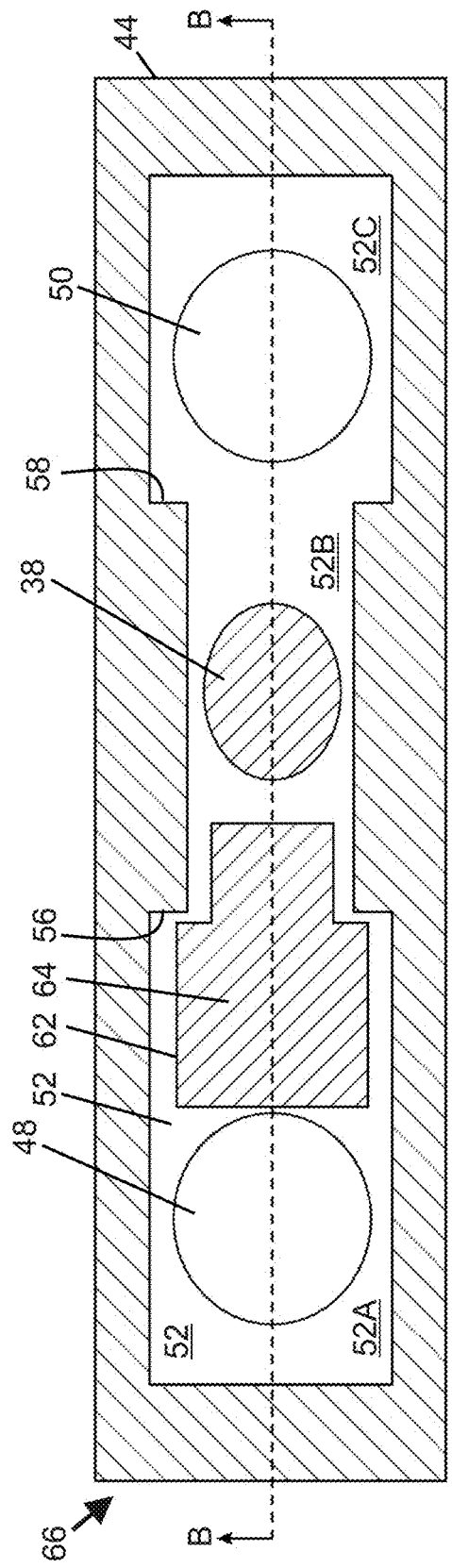
FIG. 5A is a schematic top plan view of a portion of a fluidic device including a fluidic passage bounded from below by a base structure incorporating a BAW resonator structure, bounded laterally by a wall structure, and bounded from above by a cover structure defining inlet and outlet ports, with a functionalized active region of the BAW resonator arranged generally between the inlet and outlet ports, and with an absorber region including functionalization material, associated with the base structure, and arranged upstream of the functionalized active region, according to one embodiment of the present disclosure.
Figure 5B:
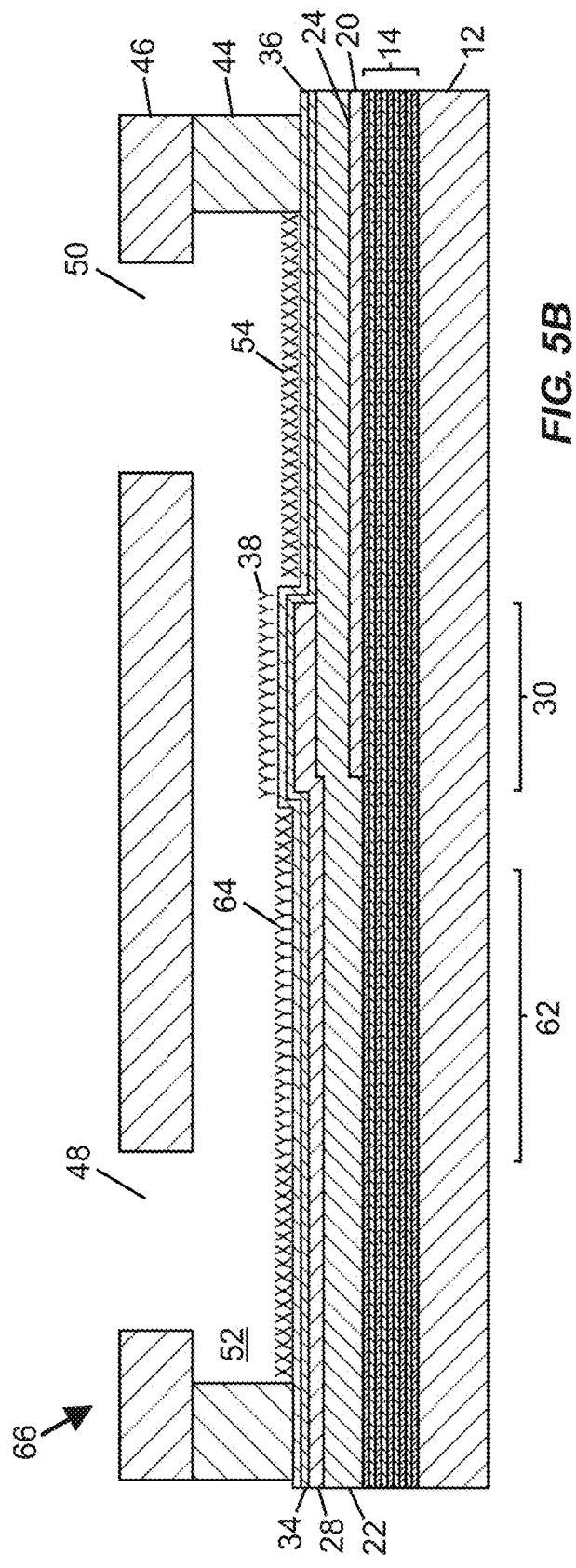
FIG. 5B is a schematic cross-sectional view of the fluidic device portion of FIG. 5A, taken along section line B-B shown in FIG. 5A, showing functionalization material associated with the functionalized active region and the absorber region, and showing blocking material arranged over other portions of the base structure non-coincident with the functionalized active and absorber regions.

FIG. 5A is a schematic top plan view, and FIG. 5B is a schematic cross-sectional view, of at least a portion of a fluidic device 66 that is similar to the device 60 shown in FIGS. 3A-4B, but with additional functionalization material 64 forming an absorber region 62. The fluidic device 66 includes a fluidic passage 52 composed of an upstream segment 52A, a narrowed width intermediate segment 52B, and a downstream segment 52C. First and second shoulder regions 56, 58 are arranged upstream and downstream, respectively, of inwardly projecting sidewall portions and define transitions (i) between the upstream segment 52A and the intermediate segment 52B, and (ii) between the intermediate segment 52B and the downstream segment 52C, respectively. The fluidic passage 52 is bounded from below by a base structure including a bulk acoustic wave (BAW) resonator structure including an active region 30, bounded laterally by a wall structure 44, and bounded from above by a cover structure 46 (which may be embodied in a cover or cap layer). The intermediate segment 52B of the fluidic passage 52 contains the active region 30, and the additional functionalization material 64 of the absorber region 62 extends within portions of the upstream segment 52A and the intermediate segment 52B. Relative to a flow of fluid that may be directed from a first fluidic port 48 through the fluidic passage 52 to a second fluidic port 50, the absorber region 62 is arranged upstream of the active region 30, and (as shown in FIG. 5A), the absorber region 62 includes an area exposed to the fluidic passage 52 that is more than two times greater than a corresponding area of functionalization material 38 overlying the active region 30.

The BAW resonator structure includes a substrate 12 overlaid with an acoustic reflector 14, and a bottom side electrode 20 arranged generally below a piezoelectric material 22. The bottom side electrode 20 is arranged along a portion of a lower surface 24 of the piezoelectric material 22. A top side electrode 28 extends over a portion of the piezoelectric material 22, wherein a portion of the piezoelectric material 22 arranged between the top side electrode 28 and the bottom side electrode 20 embodies the active region 30 of the BAW resonator structure. An interface layer 34 and a SAM 36 are provided over the top side electrode 28 and the piezoelectric material 22. In certain embodiments, a hermeticity layer (not shown) may be arranged under the interface layer 34. A portion of the SAM 36 registered with the active region 30 is overlaid with a layer of functionalization (e.g., specific binding) material 38 arranged to bind at least one analyte. Another portion of the SAM 36 upstream of, and non-coincident with, the active region 30 includes the additional functionalization material 64 to define the absorber region 62, which is laterally displaced in an upstream direction relative to the active region 30. As shown in FIG. 5B, a chemical or biological blocking material 54 is arranged over the remaining portions of the SAM 36 non-coincident with the functionalization material 38 overlying the active region 30 and non-coincident with the additional functionalization material 64 of the absorber region 62. The wall structure 44 includes walls that are laterally displaced from the active region 30 and the absorber region 62, and that extend upward from the interface layer 34 to define lateral boundaries of the fluidic passage 52. In certain embodiments, the chemical or biological blocking material 54, functionalization material 38 and additional functionalization material 64 may be deposited over portions of the base structure prior to addition of the wall structure 44 over the base structure and/or prior to addition of the cover structure 46 over the wall structure 44.

Figure 6A:
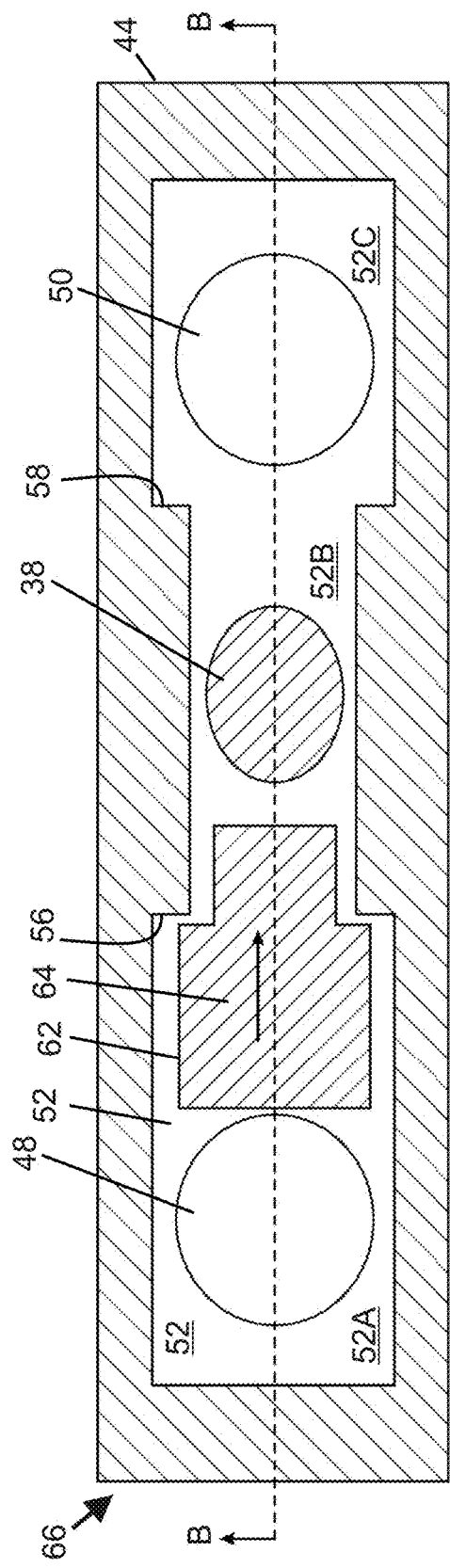
FIG. 6A is a schematic top plan view of the fluidic device portion of FIGS. 5A and 5B with a fluidic sample flowing within the fluidic passage over the functionalized active region.
Figure 6B:
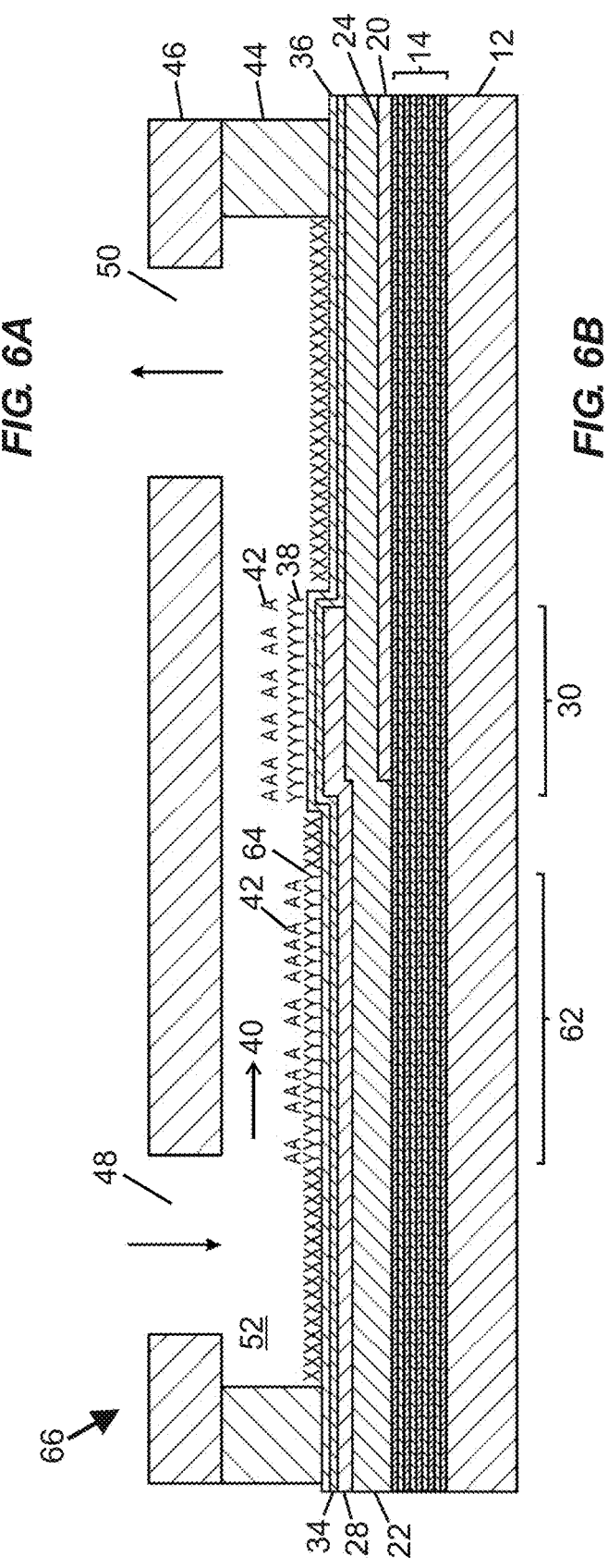
FIG. 6B is a schematic cross-sectional view of the fluidic device portion of FIGS. 5A, 5B, and 6A, taken along section line B-B shown in FIG. 6A, with a fluidic sample flowing within the fluidic passage over the absorber region and the functionalized active region, and with analyte material bound to functionalization material of the absorber region and the functionalized active region.

FIG. 6A provides a schematic top plan view, and FIG. 6B provides a schematic cross-sectional view, of the at least a portion of a fluidic device 66 of FIGS. 5A and 5B in operation. A fluid volume 40 (e.g., a fluidic sample) is supplied through the first fluidic port 48 into the upstream segment 52A of the fluidic passage 52, over the absorber region 62 straddling the upstream segment 52A and the intermediate segment 52B, then over the active region 30, and then into the downstream segment 52C to the second fluidic port 50 to exit the fluidic passage 52. As shown in FIG. 6B, analyte 42 from the fluid volume 40 is bound to the additional functionalization material 64 of the absorber region 62, and is further bound to the functionalization material 38 overlying the active region 30, but neither the additional functionalization material 64 nor the functionalization material 38 is saturated, since less than all binding sites are occupied with analyte 42 in each instance. When a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte 42 bound to the functionalization material 38. Presence of the absorber region 62 with additional functionalization material 64 upstream of the functionalization material 38 that overlies the active region 30 functions to bind a portion of analyte 42 from the fluid volume 40 that would otherwise result in saturation of the functionalization material 38 overlying the active region 30 if the absorber region 62 were omitted. In this regard, the absorber region 62 serves to increase the dynamic measurement range of the fluidic device 66 by reducing the likelihood of saturation of the functionalization material 38 overlying the active region 30.

In certain embodiments, multiple absorber regions may be provided in a fluidic device incorporating one or more BAW resonator structures and/or one or more absorber regions may be arranged on surfaces other than a base structure of a fluidic device incorporating one or more BAW resonator structures.

FIG. 7A is a schematic top plan view, and FIG. 7B is a schematic cross-sectional view, of at least a portion of a fluidic device 76 including multiple absorber regions 62, 70, 74 associated with a base structure, a wall structure 44, and a cover structure 46 (e.g., a cover or cap layer), respectively. The fluidic device 76 includes a fluidic passage 52 that is bounded from below by a base structure, which incorporates a BAW resonator structure. The fluidic passage 52 is also bounded laterally by the wall structure 44 and is bounded from above by the cover structure 46, which defines first and second fluidic ports 48, 50. The fluidic passage 52 is composed of an upstream segment 52A, a narrowed width intermediate segment 52B (which contains an active region 30), and a downstream segment 52C. First and second shoulder regions 56, 58 are arranged upstream and downstream, respectively, of inwardly projecting sidewall portions and define transitions (i) between the upstream segment 52A and the intermediate segment 52B, and (ii) between the intermediate segment 52B and the downstream segment 52C, respectively.

The BAW resonator structure includes a substrate 12 overlaid with an acoustic reflector 14, and a bottom side electrode 20 arranged generally below a piezoelectric material 22. The bottom side electrode 20 is arranged along a portion of a lower surface 24 of the piezoelectric material 22. A top side electrode 28 extends over a portion of the piezoelectric material 22, wherein a portion of the piezoelectric material 22 arranged between the top side electrode 28 and the bottom side electrode 20 embodies the active region 30 of the BAW resonator structure. An interface layer 34 and a first SAM 36 are provided over the top side electrode 28 and the piezoelectric material 22. A portion of the first SAM 36 registered with the active region 30 is overlaid with a layer of functionalization (e.g., specific binding) material 38 to yield the (functionalized) active region 30, with the functionalization material 38 arranged to bind at least one analyte borne by a fluid volume 40 within the fluidic passage 52. Another portion of the first SAM 36 arranged upstream of the active region 30 is overlaid with additional functionalization material 64 to form a first absorber region 62 associated with the base structure. Portions of the first SAM 36 non-coincident with the active region 30 and non-coincident with the first absorber region 62 are overlaid with a chemical or biological blocking material 54 to prevent localized attachment of functionalization material and/or analyte.

With reference to FIG. 7A, lateral portions of the wall structure 44 in the upstream segment 52A of the fluidic passage 52 include a second SAM 68, with one portion of the second SAM 68 being overlaid with a chemical or biological blocking material 54 (to prevent localized attachment of functionalization material and/or analyte) and another portion of the second SAM 68 being overlaid with additional functionalization material 64 to form a second absorber region 70. With reference to FIG. 7B, a lower surface of the cover structure 46 is overlaid with a third SAM 72, with one portion of the third SAM 72 being overlaid with a chemical or biological blocking material 54, and another portion of the third SAM 72 being overlaid with additional functionalization material 64 to form a third absorber region 74. Each absorber region 62, 70, 74 is arranged upstream of the active region 30. In certain embodiments, each absorber region 62, 70, 74 includes additional functionalization material 64 of the same composition, concentration, and/or amount. In other embodiments, one or more of the foregoing may differ. In certain embodiments, each absorber region 62, 70, 74 may include additional functionalization material 64 having the same composition and/or concentration as functionalization material 38 of the active region 30. In other embodiments, one or more absorber region 62, 70, 74 may include additional functionalization material 64 having a composition and/or concentration that differs from functionalization material 38 of the active region 30.

In certain embodiments, one or more absorber regions may include non-specific binding material, whereas one or more functionalized active regions may include specific binding material. In certain embodiments, absorber regions and functionalized active regions may all include specific binding material (e.g., of the same composition or different composition), or may all include non-specific binding material (e.g., of the same composition or different composition).

In operation of the fluidic device 76, the fluid volume 40 (e.g., a fluidic sample) is supplied through the first fluidic port 48 into the upstream segment 52A of the fluidic passage 52, over the absorber regions 62, 70, 74 straddling the upstream segment 52A and the intermediate segment 52B, then over the active region 30, and then into the downstream segment 52C to the second fluidic port 50 to exit the fluidic passage 52. Analyte (not shown) from the fluid volume 40 may be bound to the additional functionalization material 64 of the absorber regions 62, 70, 74, and may be further bound to the functionalization material 38 overlying the active region 30. Saturation of the functionalization material 38 overlying the active region 30 should be delayed until after the absorber regions 62, 70, 74 are saturated with analyte. In this regard, the absorber regions 62, 70, 74 will serve to increase the dynamic measurement range of the fluidic device 76 by reducing the likelihood of saturation of the functionalization material 38 overlying the active region 30. When a bulk acoustic wave having a dominant shear component is induced in the active region 30 by supplying an electrical (e.g., alternating current) signal of a desired frequency to the bottom and top side electrodes 20, 28, a change in electroacoustic response (e.g., at least one of an amplitude-magnitude property, a frequency property, or a phase property, such as a shift in resonant frequency) of the BAW resonator structure may be detected to indicate a presence and/or quantity of analyte bound to the functionalization material 38.

In certain embodiments, multiple absorber regions and multiple active regions may be placed in sequence, with alternating placement of absorber regions and functionalized active regions.

Figure 8:
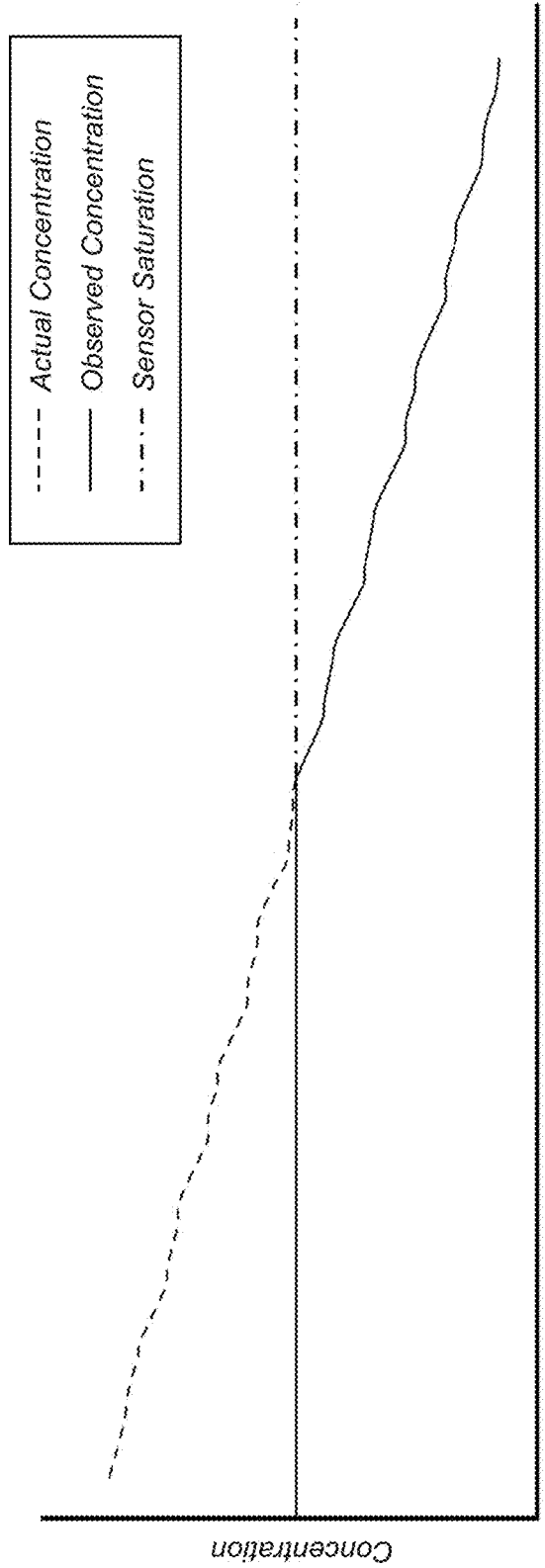
FIG. 8 is a plot of observed concentration and actual concentration versus position for a fluidic device (illustrated in FIG. 9) incorporating ten BAW resonator structures with ten functionalized active regions and ten absorber regions including functionalization material arranged in sequence within a fluidic passage, with alternating placement of absorber regions and functionalized active regions, and with a discrepancy between observed concentration and the actual concentration showing that the first five functionalized active regions are saturated with analyte.

FIG. 8 is a plot of observed concentration and actual concentration versus position for a fluidic device (to be discussed hereinafter in connection with FIG. 9 and FIGS. 10A-10E) incorporating ten BAW resonator structures with ten functionalized active regions and ten absorber regions including functionalization material arranged in sequence within a fluidic passage, with alternating placement of absorber regions and functionalized active regions useable to interact with analyte present in a fluid volume (e.g., a fluid sample). Three different line types (i.e., dashed corresponding to actual analyte concentration, solid corresponding to observed analyte concentration, and dot-dash corresponding to a sensor saturation condition) are illustrated. In the left half of FIG. 8 corresponding to the first five active regions of the fluidic device, the observed analyte concentration (represented by a solid line) is less than the actual analyte concentration, since functionalization material of the first five active regions is fully saturated with analyte. In the right half of FIG. 8 corresponding to the second five active regions of the fluidic device, the observed analyte concentration corresponds to the actual analyte concentration because the actual concentration is below a threshold (indicated by the horizontal dot-dash-line) for saturation of functionalization material associated with the active regions. The general downward trend of the actual analyte concentration in the fluid volume is attributable to binding of analyte to functionalization material of active regions and absorber regions as the fluid volume flows through a fluidic passage containing such regions. FIG. 8 therefore shows that utilization of multiple serially arranged functionalized active regions with interspersed absorber regions may beneficially increase the dynamic measurement range of a BAW resonator-based fluidic sensing device, by reducing the likelihood that all functionalized active regions will be saturated for a given analyte concentration.

Figure 9:
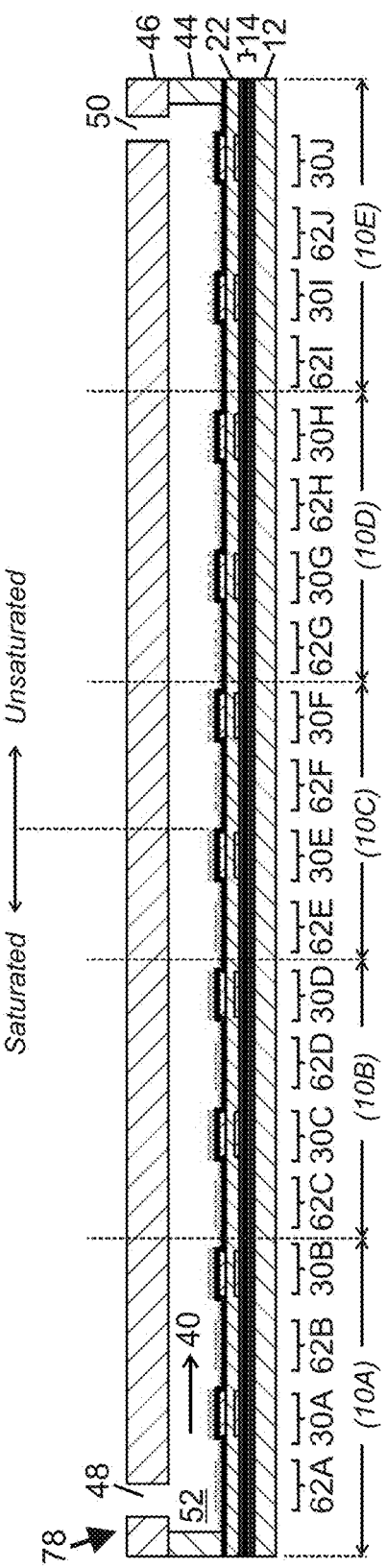
FIG. 9 is a schematic cross-sectional view of at least a portion of a fluidic device incorporating ten BAW resonator structures with ten functionalized active regions and ten absorber regions including functionalization material arranged in sequence within a fluidic passage, with alternating placement of absorber regions and functionalized active regions, and with the first five absorber regions and functionalized active regions being saturated with analyte, and the remaining five absorber regions and functionalized active regions including declining amounts of bound analyte.

FIG. 9 is a schematic cross-sectional view of at least a portion of a fluidic device 78 incorporating ten BAW resonator structures with ten functionalized active regions 30A-30J and ten absorber regions 62A-62J (each including functionalization material) sequentially arranged within a fluidic passage 52 arranged to receive a fluid volume 40, with alternating placement of absorber regions 62A-62J and functionalized active regions 30A-30J, with the first five absorber regions 62A-62E and functionalized active regions 30A-30E being saturated with analyte, and with the second five absorber regions 62F-62J and functionalized active regions 30F-30J including declining amounts of bound analyte. The fluidic device 78 includes a substrate 12, an acoustic reflector 14 arranged over the substrate 12, a piezoelectric material 22, a wall structure 44, and a cover structure 46 that defines first and second fluidic ports 48, 50. Since certain features of FIG. 9 are too small to be clearly seen, FIGS. 10A-10E provide magnified schematic cross-sectional views of portions of the fluidic device 78 of FIG. 9, with such portions being indicated between dashed line segments in FIG. 9 and labeled as (10A) to (10E) respectively.

Figure 10A:
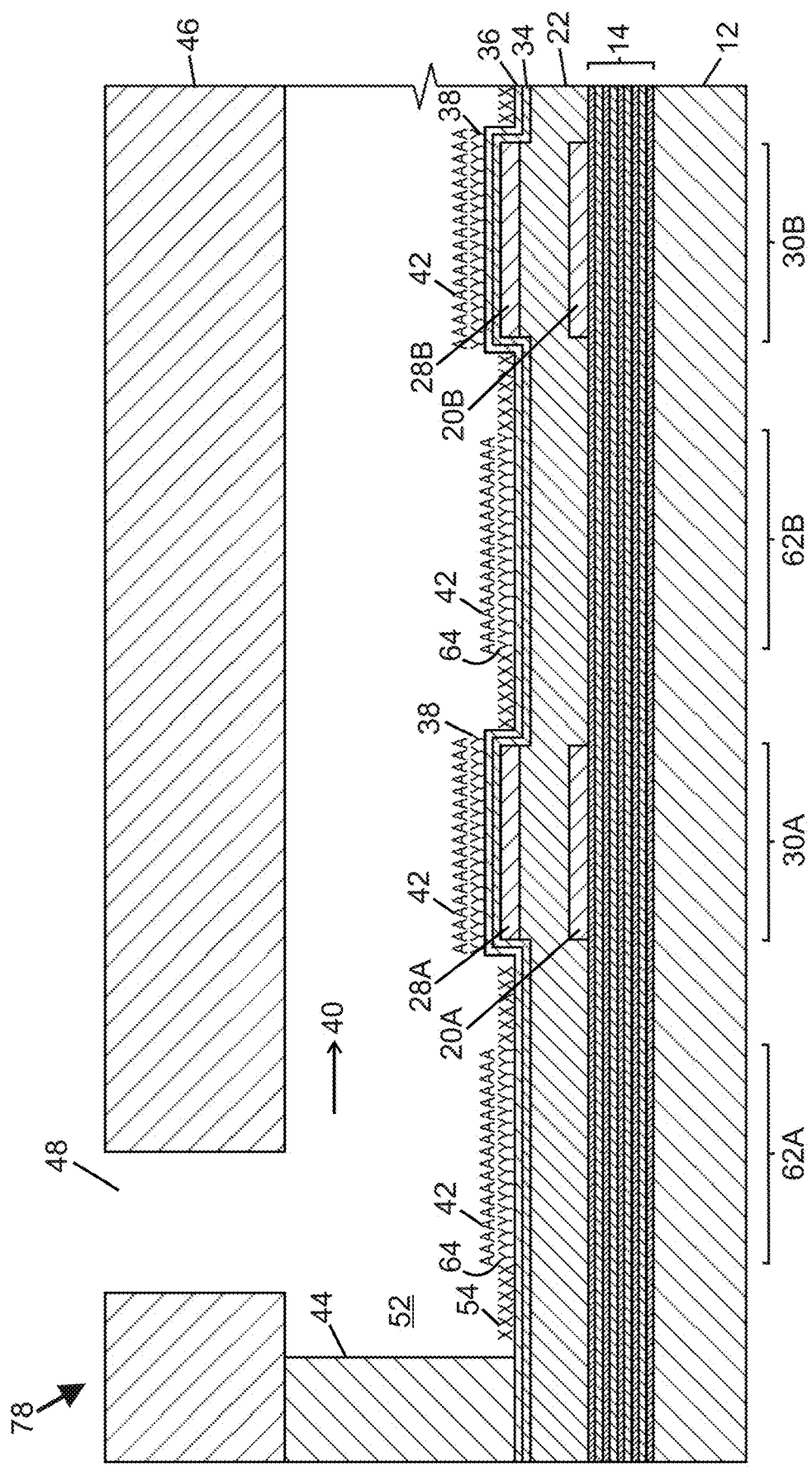
FIGS. 10A-10E are magnified schematic cross-sectional views of portions of the fluidic device of FIG. 9.

FIG. 10A is a magnified schematic cross-sectional view of a first portion of the fluidic device 78 of FIG. 9, including first and second absorber regions 62A, 62B and active regions 30A, 30B as well as a left portion of the wall structure 44, and the first fluidic port 48 defined in the cover structure 46. Bottom side electrodes 20A, 20B and top side electrodes 28A, 28B are arranged below and above the piezoelectric material 22, respectively, with areas in which piezoelectric material 22 is arranged between overlapping areas of the electrodes 20A, 20B, 28A, 28B forming the active regions 30A, 30B. The top side electrodes 28A, 28B and the piezoelectric material 22 are overlaid with an interface layer 34 and a self-assembled monolayer (SAM) 36. Portions of the SAM 36 registered with the active regions 30A, 30B are overlaid with a layer of functionalization (e.g., specific binding) material 38 to yield functionalized active regions 30A, 30B, with the functionalization material 38 arranged to bind at least one analyte 42 borne by a fluid volume 40 within the fluidic passage 52. Further portions of the SAM 36 arranged upstream of each active region 30A, 30B are overlaid with additional functionalization material 64 to form absorber regions 62A, 62B. Still further portions of the SAM 36 non-coincident with the active regions 30A, 30B and non-coincident with the absorber regions 62A, 62B are overlaid with a chemical or biological blocking material 54 to prevent localized attachment of functionalization material and/or analyte.

Figure 10B:
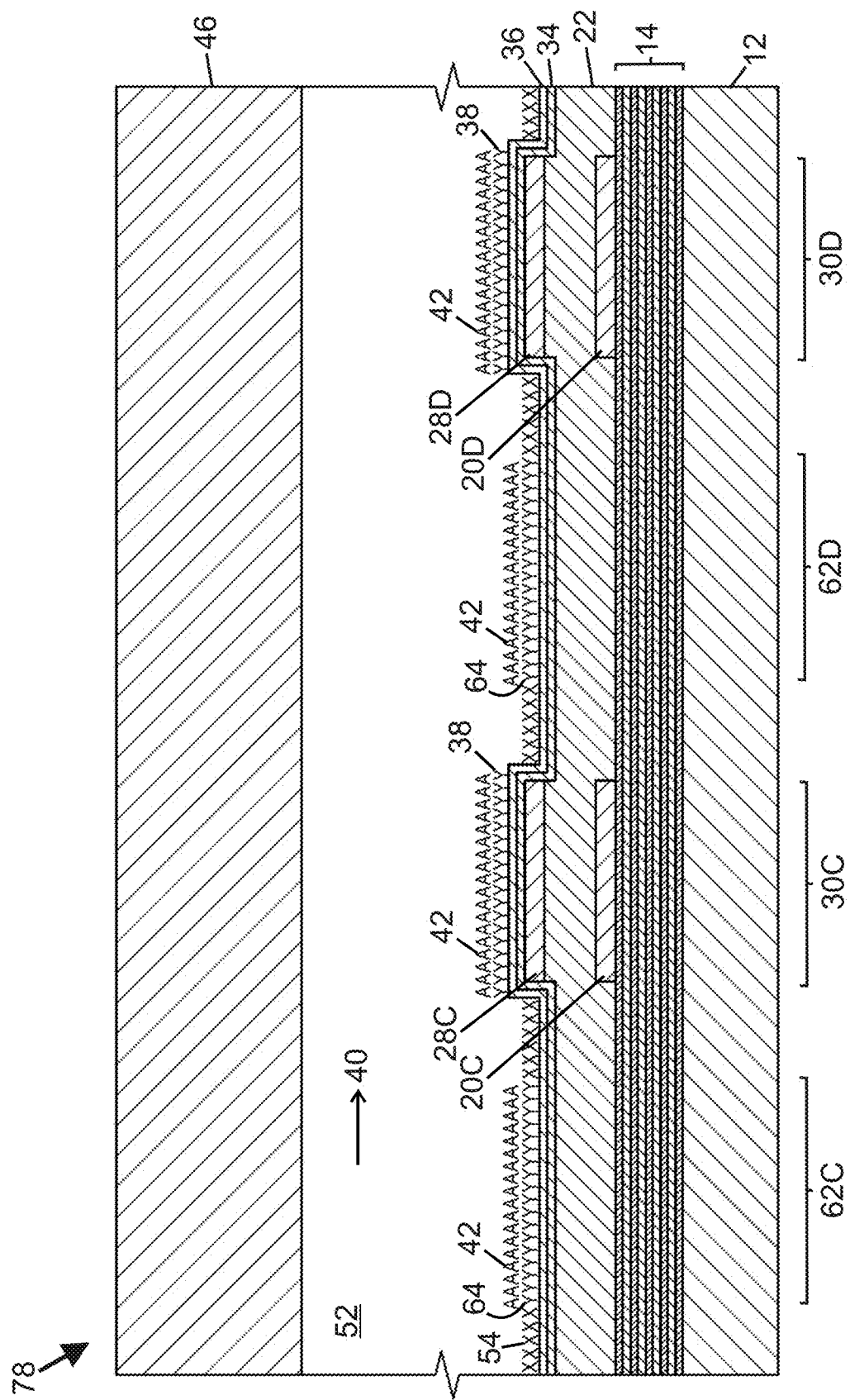

FIG. 10B is a magnified schematic cross-sectional view of a second portion of the fluidic device 78 of FIG. 9 including third and fourth absorber regions 62C, 62D and active regions 30C, 30D. Bottom side electrodes 20C, 20D and top side electrodes 28C, 28D are arranged below and above the piezoelectric material 22, respectively, with areas in which piezoelectric material 22 is arranged between overlapping areas of the electrodes 20C, 20D, 28C, 28D forming the active regions 30C, 30D. The top side electrodes 28C, 28D and the piezoelectric material 22 are overlaid with an interface layer 34 and a self-assembled monolayer (SAM) 36. Portions of the SAM 36 registered with the active regions 30C, 30D are overlaid with a layer of functionalization (e.g., specific binding) material 38 to yield functionalized active regions 30C, 30D, with the functionalization material 38 arranged to bind at least one analyte 42 borne by a fluid volume 40 within the fluidic passage 52. Further portions of the SAM 36 arranged upstream of each active region 30C, 30D are overlaid with additional functionalization material 64 to form absorber regions 62C, 62D. Still further portions of the SAM 36 non-coincident with the active regions 30C, 30D and non-coincident with the absorber regions 62C, 62D are overlaid with a chemical or biological blocking material 54 to prevent localized attachment of functionalization material and/or analyte.

Figure 10C:
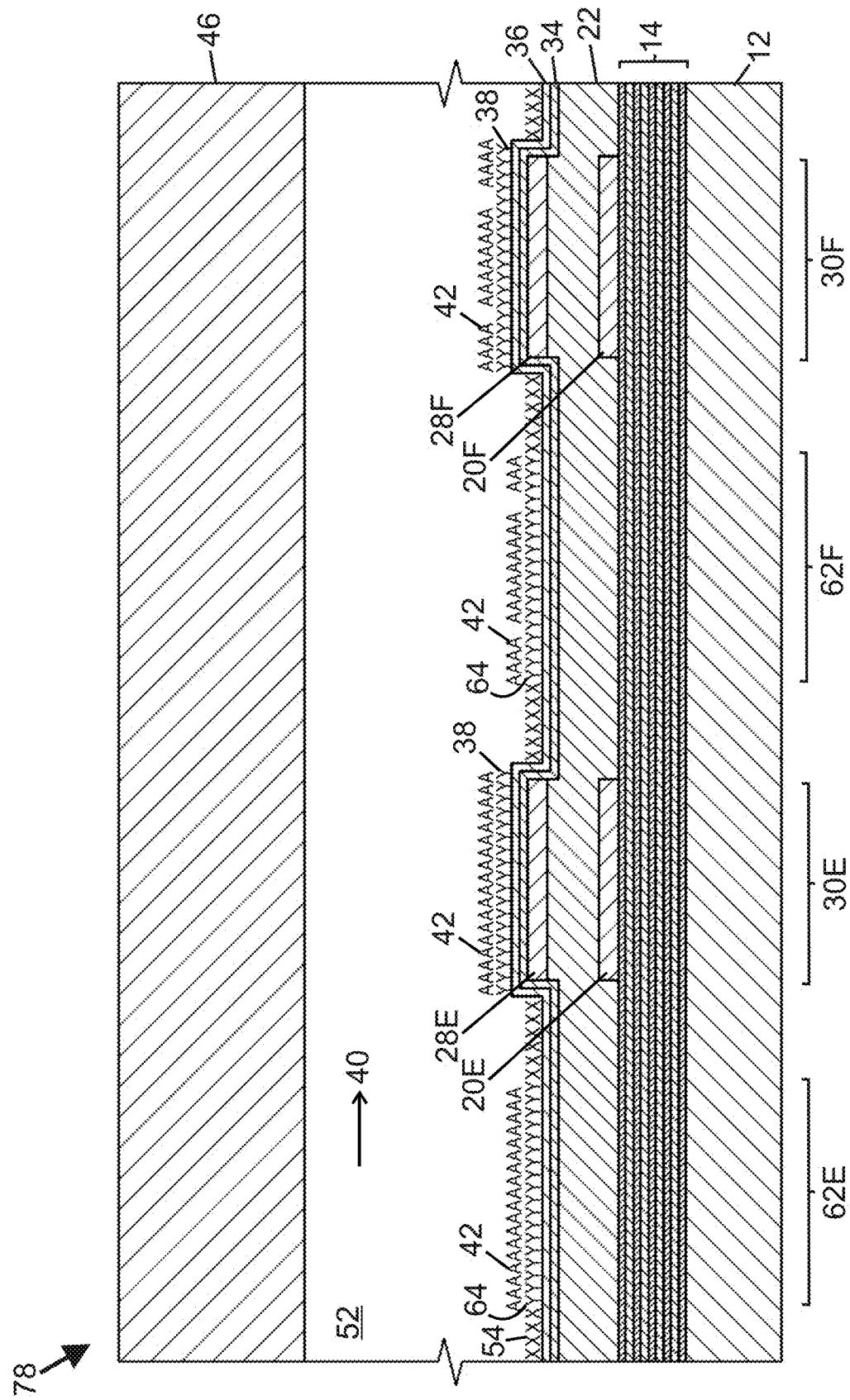

FIG. 10C is a magnified schematic cross-sectional view of a third portion of the fluidic device 78 of FIG. 9 including fifth and sixth absorber regions 62E, 62F and active regions 30E, 30F. Bottom side electrodes 20E, 20F and top side electrodes 28E, 28F are arranged below and above the piezoelectric material 22, respectively, with areas in which piezoelectric material 22 is arranged between overlapping areas of the electrodes 20E, 20F, 28E, 28F forming the active regions 30E, 30F. The top side electrodes 28E, 28F and the piezoelectric material 22 are overlaid with an interface layer 34 and a self-assembled monolayer (SAM) 36. Portions of the SAM 36 registered with the active regions 30E, 30F are overlaid with a layer of functionalization (e.g., specific binding) material 38 to yield functionalized active regions 30E, 30F, with the functionalization material 38 arranged to bind at least one analyte 42 borne by a fluid volume 40 within the fluidic passage 52. Further portions of the SAM 36 arranged upstream of each active region 30E, 30F are overlaid with additional functionalization material 64 to form absorber regions 62E, 62F. Still further portions of the SAM 36 non-coincident with the active regions 30E, 30F and non-coincident with the absorber regions 62E, 62F are overlaid with a chemical or biological blocking material 54 to prevent localized attachment of functionalization material and/or analyte.

Figure 10D:
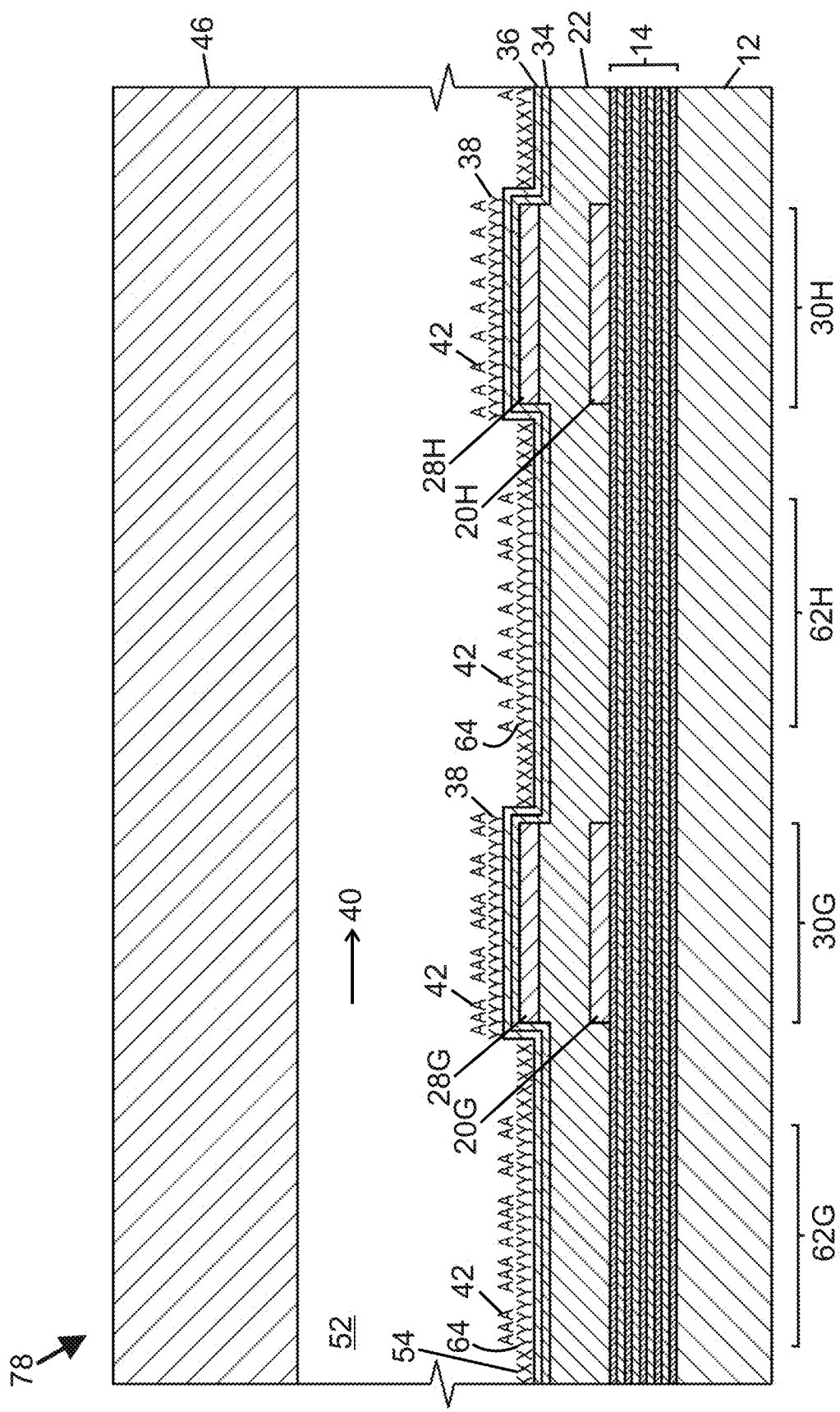

FIG. 10D is a magnified schematic cross-sectional view of a fourth portion of the fluidic device 78 of FIG. 9 including seventh and eighth absorber regions 62G, 62H and active regions 30G, 30H. Bottom side electrodes 20G, 20H and top side electrodes 28G, 28H are arranged below and above the piezoelectric material 22, respectively, with areas in which piezoelectric material 22 is arranged between overlapping areas of the electrodes 20G, 20H, 28G, 28H forming the active regions 30G, 30H. The top side electrodes 28G, 28H and the piezoelectric material 22 are overlaid with an interface layer 34 and a self-assembled monolayer (SAM) 36. Portions of the SAM 36 registered with the active regions 30G, 30H are overlaid with a layer of functionalization (e.g., specific binding) material 38 to yield functionalized active regions 30G, 30H, with the functionalization material 38 arranged to bind at least one analyte 42 borne by a fluid volume 40 within the fluidic passage 52. Further portions of the SAM 36 arranged upstream of each active region 30G, 30H are overlaid with additional functionalization material 64 to form absorber regions 62G, 62H. Still further portions of the SAM 36 non-coincident with the active regions 30G, 30H and non-coincident with the absorber regions 62G, 62H are overlaid with a chemical or biological blocking material 54 to prevent localized attachment of functionalization material and/or analyte.

Figure 10E:
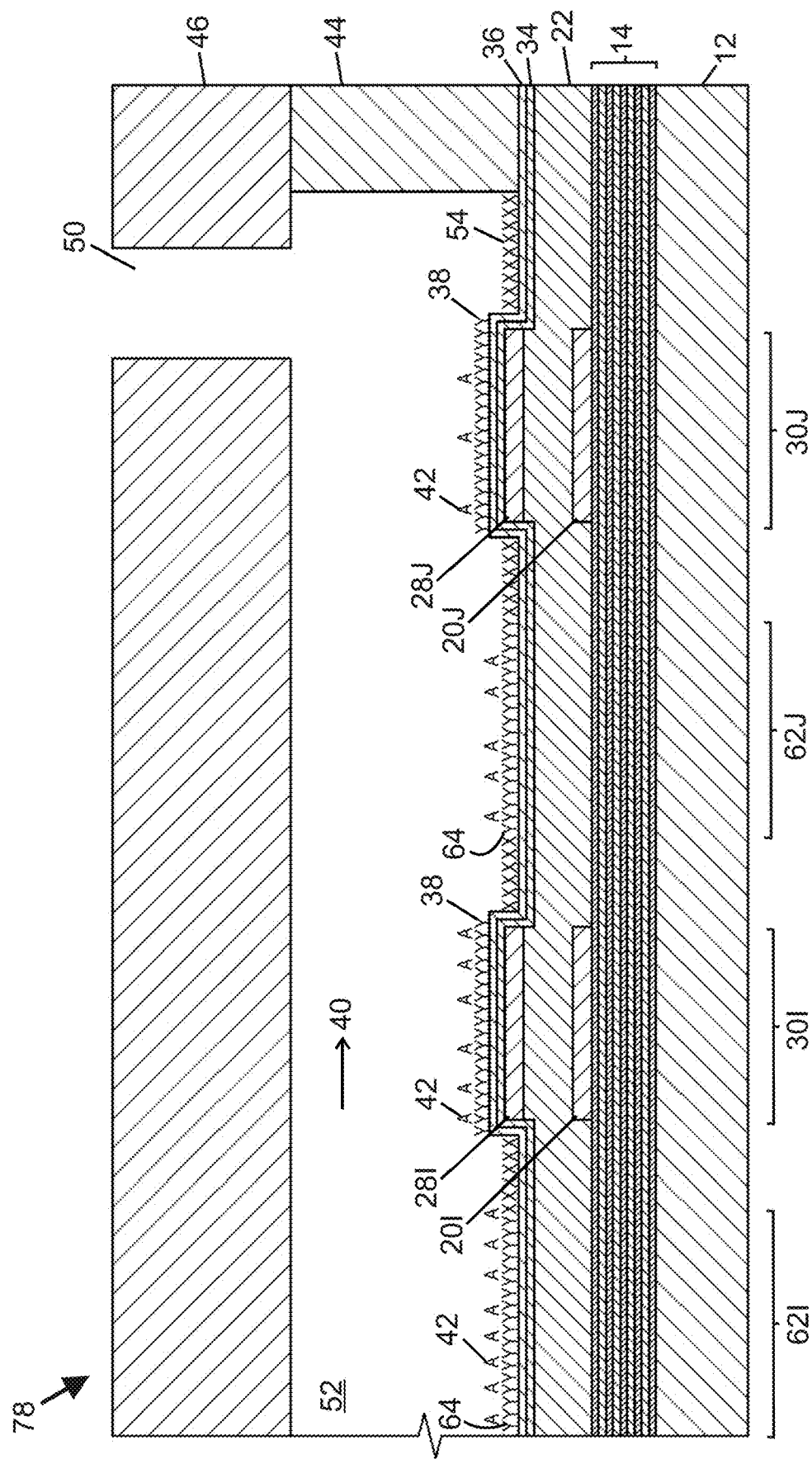

FIG. 10E is a magnified schematic cross-sectional view of a fifth portion of the fluidic device 78 of FIG. 9 including ninth and tenth absorber regions 62I, 62J and active regions 30I, 30J as well as a right portion of the wall structure 44, and a second fluidic port 50 defined in the cover structure 46. Bottom side electrodes 20I, 20J and top side electrodes 28I, 28J are arranged below and above the piezoelectric material 22, respectively, with areas in which piezoelectric material 22 is arranged between overlapping areas of the electrodes 20I, 20J, 28I, 28J forming the active regions 30I, 30J. The top side electrodes 28I, 28J and the piezoelectric material 22 are overlaid with an interface layer 34 and a self-assembled monolayer (SAM) 36. Portions of the SAM 36 registered with the active regions 30I, 30J are overlaid with a layer of functionalization (e.g., specific binding) material 38 to yield functionalized active regions 30I, 30J, with the functionalization material 38 arranged to bind at least one analyte 42 borne by a fluid volume 40 within the fluidic passage 52. Further portions of the SAM 36 arranged upstream of each active region 30I, 30J are overlaid with additional functionalization material 64 to form absorber regions 62I, 62J. Still further portions of the SAM 36 non-coincident with the active regions 30I, 30J and non-coincident with the absorber regions 62I, 62J are overlaid with a chemical or biological blocking material 54 to prevent localized attachment of functionalization material and/or analyte.

With reference to FIGS. 9 and 10A-10E, during operation of the fluidic device 78, the fluid volume 40 containing analyte is supplied to the fluidic passage 52, and a bulk acoustic wave having a dominant shear component is induced in each active region 30A-30J by supplying an electrical (e.g., alternating current) signal of a desired frequency to each pair of bottom and top side electrodes 20A-20J, 28A-20J. A change in electroacoustic response (e.g., at least one of an amplitude-magnitude property, a frequency property, or a phase property, such as a shift in resonant frequency) of the BAW resonator structure of each active region 30A-30J may be detected to indicate a presence and/or quantity of analyte 42 bound to the functionalization material 38 of each active region 30A-30J. As shown in FIG. 9 and FIGS. 10A-10E, when the fluid volume 40 contains a relatively high concentration of analyte, functionalization material 38, 64 of the first five absorbers 62A-62E and the first five active regions 30A-30E, respectively, becomes saturated with analyte 42 bound thereto (such that all binding sites of the functionalization material 38, 64 are occupied with analyte 42). Due to this condition, the observed concentration of analyte 42 bound to the first five active regions 30A-30E is less than the actual concentration of analyte in the fluid volume 40, as shown in the left half of FIG. 8. However, the presence of multiple absorber regions 62A-62J and active regions 30A-30J including functionalization material 38, 64 causes analyte 38 to be depleted from the fluid volume 40, such that the second five active regions 30F-30J and absorber regions 62F-62J have a declining amount of bound analyte 42 and are not saturated with analyte 42. As a result, signals corresponding to actual analyte concentration can be obtained from the second five active regions 30F-30J. Thus, alternating serial arrangement of multiple absorber regions 62A-62J and active regions 30A-30J serves to increase the dynamic measurement range of the fluidic device 78 by reducing the likelihood that functionalization material 38 associated with every single active region 30A-30J will be fully saturated for a fluid volume 40 having a given analyte concentration.

Although ten active regions 30A-30J and ten absorbers 62A-62J were illustrated in FIG. 9 and FIGS. 10A-10E, it is to be appreciated that any suitable number of active regions and absorber regions may be provided, and the number of absorbers may or may not equal the number of active regions. In certain embodiments, the aggregate area of one or more absorber regions exposed to a fluid volume in a single fluidic passage may exceed an aggregate area of one or more active regions exposed to the fluid volume in the same fluidic passage.

Figure 11A:
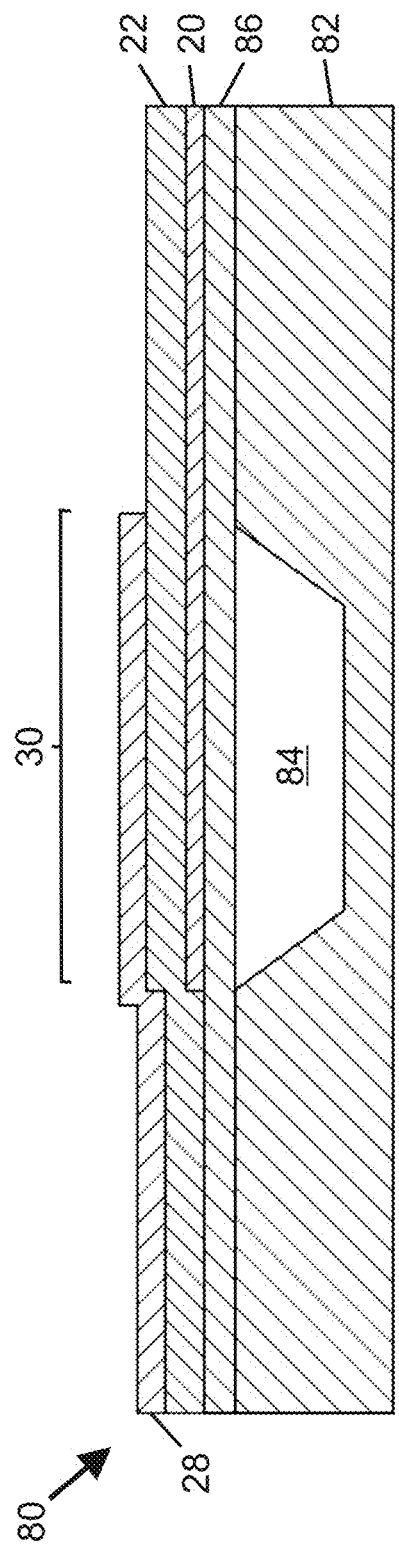
FIG. 11A is a schematic cross-sectional view of a film bulk acoustic wave resonator (FBAR) structure usable in devices according to certain embodiments, with the FBAR structure including an inclined c-axis hexagonal crystal structure piezoelectric material, a substrate defining a cavity optionally covered by a support layer, and an active region registered with the cavity, with a portion of the piezoelectric material arranged between overlapping portions of a top side electrode and a bottom side electrode.

FIG. 11A is a schematic cross-sectional view of a film bulk acoustic wave resonator (FBAR) structure 80 including an active region 30, wherein at least portions of the active region 30 are subject to being overlaid with an interface layer and a self-assembled monolayer (SAM) suitable for receiving a functionalization (e.g., specific binding or non-specific binding) material to form at least one functionalized active region (not shown) and at least one functionalized absorber region (not shown) according to one embodiment. The FBAR structure 80 includes a substrate 82 (e.g., silicon or another semiconductor material) defining a cavity 84 optionally covered by a support layer 86 (e.g., silicon dioxide). A bottom side electrode 20 is arranged over a portion of the support layer 86, a piezoelectric material 22, preferably embodying inclined c-axis hexagonal crystal structure piezoelectric material (e.g., AlN or ZnO), is arranged over the bottom side electrode 20 and the support layer 86, and a top side electrode 28 is arranged over at least a portion of a top surface of the piezoelectric material 22. A portion of the piezoelectric material 22 arranged between the top side electrode 28 and the bottom side electrode 20 embodies the active region 30 of the FBAR structure 80. The active region 30 is arranged over and registered with the cavity 84 disposed below the support layer 86. The cavity 84 serves to confine acoustic waves induced in the active region 30 by preventing dissipation of acoustic energy into the substrate 82, since acoustic waves do not efficiently propagate across the cavity 84. In this respect, the cavity 84 provides an alternative to the acoustic reflector 14 illustrated in FIGS. 1, 3B, 4B, 5B, 6B, 7B, 9 and 10A-10E. Although the cavity 84 shown in FIG. 11A is bounded from below by a thinned portion of the substrate 82, in alternative embodiments at least a portion of the cavity 84 may extend through an entire thickness of the substrate 82. Steps for forming the FBAR structure 80 may include defining the cavity 84 in the substrate 82, filling the cavity 84 with a sacrificial material (not shown) optionally followed by planarization of the sacrificial material, depositing the support layer 86 over the substrate 82 and the sacrificial material, removing the sacrificial material (e.g., by flowing an etchant through vertical openings defined in the substrate 82 or the support layer 86, or lateral edges of the substrate 82), depositing the bottom side electrode 20 over the support layer 86, growing (e.g., via sputtering or other appropriate methods) the piezoelectric material 22, and depositing the top side electrode 28. In certain embodiments, the top side electrode 28, piezoelectric material 22, and the bottom side electrode 20 in combination may be self-supporting, and the support layer 86 may be omitted and/or removed by etching in the vicinity of the active region 30.

Figure 11B:
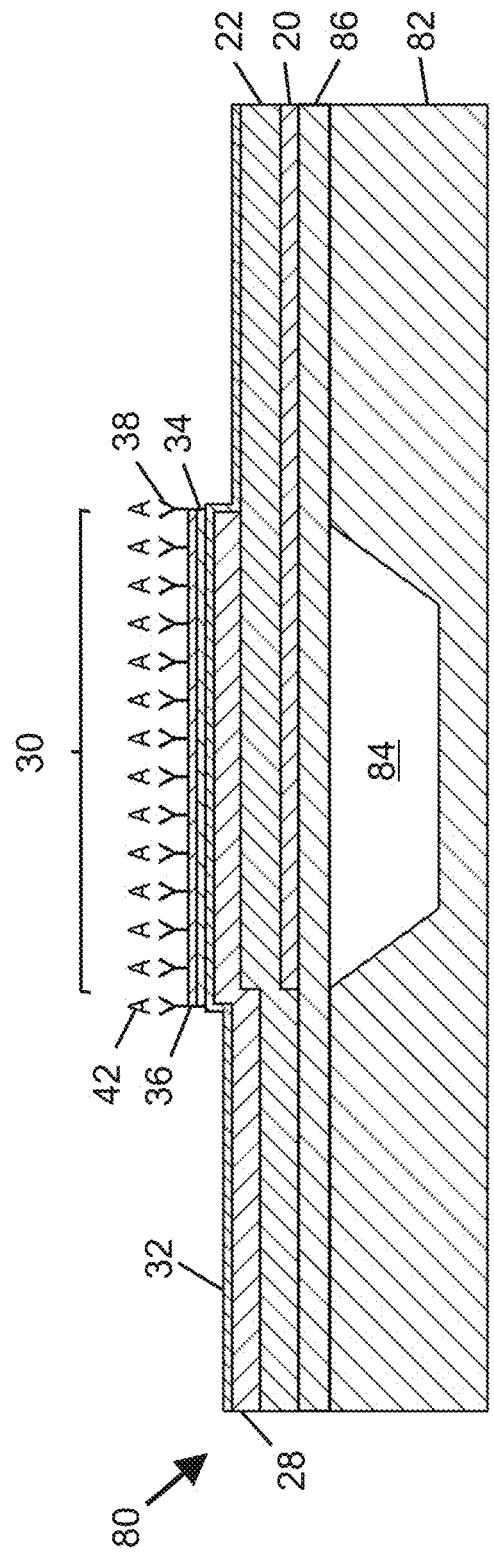
FIG. 11B is a schematic cross-sectional view of the FBAR structure according to FIG. 11A, following addition of a hermeticity layer, an interface layer, a self-assembled monolayer, and a functionalization (e.g., specific binding) material over at least portions of the FBAR structure.

FIG. 11B is a schematic cross-sectional view of the FBAR structure 80 according to FIG. 11A, following addition of a hermeticity layer 32, an interface layer 34, a self-assembled monolayer 36, and functionalization material 38 (e.g., specific binding material). The hermeticity layer 32 is arranged over the entire piezoelectric material 22 (as well as the top side electrode 28), whereas the functionalization material 38, the SAM 36, and the interface layer 34 are arranged solely over the active region 30. As shown in FIG. 11B, analyte 42 is bound to the functionalization material 38, such as may occur following exposure of the functionalization material 38 to a medium (e.g., liquid or other fluid) containing the analyte 42, optionally as part of a microfluidic device. It is to be appreciated that in the context of a fluidic device, additional functionalization material (not shown) may be provided over portions of the SAM 36 upstream of the active region 30 to form at least one absorber (not shown).

As will be recognized by one skilled in the art upon review of the present disclosure, in certain embodiments, the FBAR structure 80 of FIGS. 11A and 11B may be substituted for the solidly mounted BAW resonator structures disclosed previously herein. In certain embodiments, the FBAR structure 80 of FIG. 11B may be incorporated in a fluidic device (e.g., microfluidic device) including one or more absorbers (including functionalization material) arranged upstream of one or more functionalized active regions.

Figure 12:
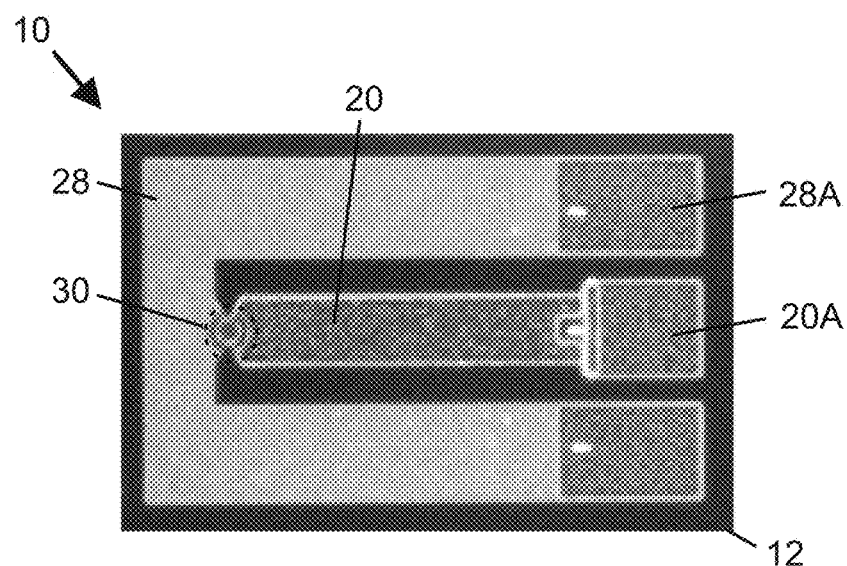
FIG. 12 is a top plan view photograph of a bulk acoustic wave MEMS resonator device suitable for receiving a hermeticity layer, an interface layer, a self-assembled monolayer, and functionalization (e.g. specific binding) material as disclosed herein.

FIG. 12 is a top plan view photograph of a bulk acoustic wave MEMS resonator device 10 (consistent with the portion of the resonator device 10 illustrated in FIG. 1) suitable for receiving a hermeticity layer, an interface layer, a self-assembled monolayer, and/or functionalization (e.g., specific binding) material as disclosed herein, wherein the MEMS resonator device 10 may serve as a base structure of a fluidic device as disclosed herein. The MEMS resonator device 10 includes a piezoelectric material (not shown) arranged over a substrate 12, a bottom side electrode 20 arranged under a portion of the piezoelectric material, and a top side electrode 28 arranged over a portion of the piezoelectric material, including an active region 30 in which the piezoelectric material is arranged between overlapping portions of the top side electrode 28 and the bottom side electrode 20. Externally accessible contacts 20A, 28A are in electrical communication with the bottom side electrode 20 and the top side electrode 28, respectively. After portions of the resonator device 10 are overlaid with an interface layer, a self-assembled monolayer, and functionalization (e.g., specific binding) material as disclosed herein, the resonator device 10 may be used as a sensor and/or incorporated into a microfluidic device. If desired, multiple resonator devices 10 may be provided in an array on a single substrate 12. Additionally, a fluidic device (e.g., microfluidic device) incorporating the MEMS resonator device 10 may include one or more absorbers (including functionalization material) as disclosed herein, arranged upstream of the active region 30.

Figure 13:
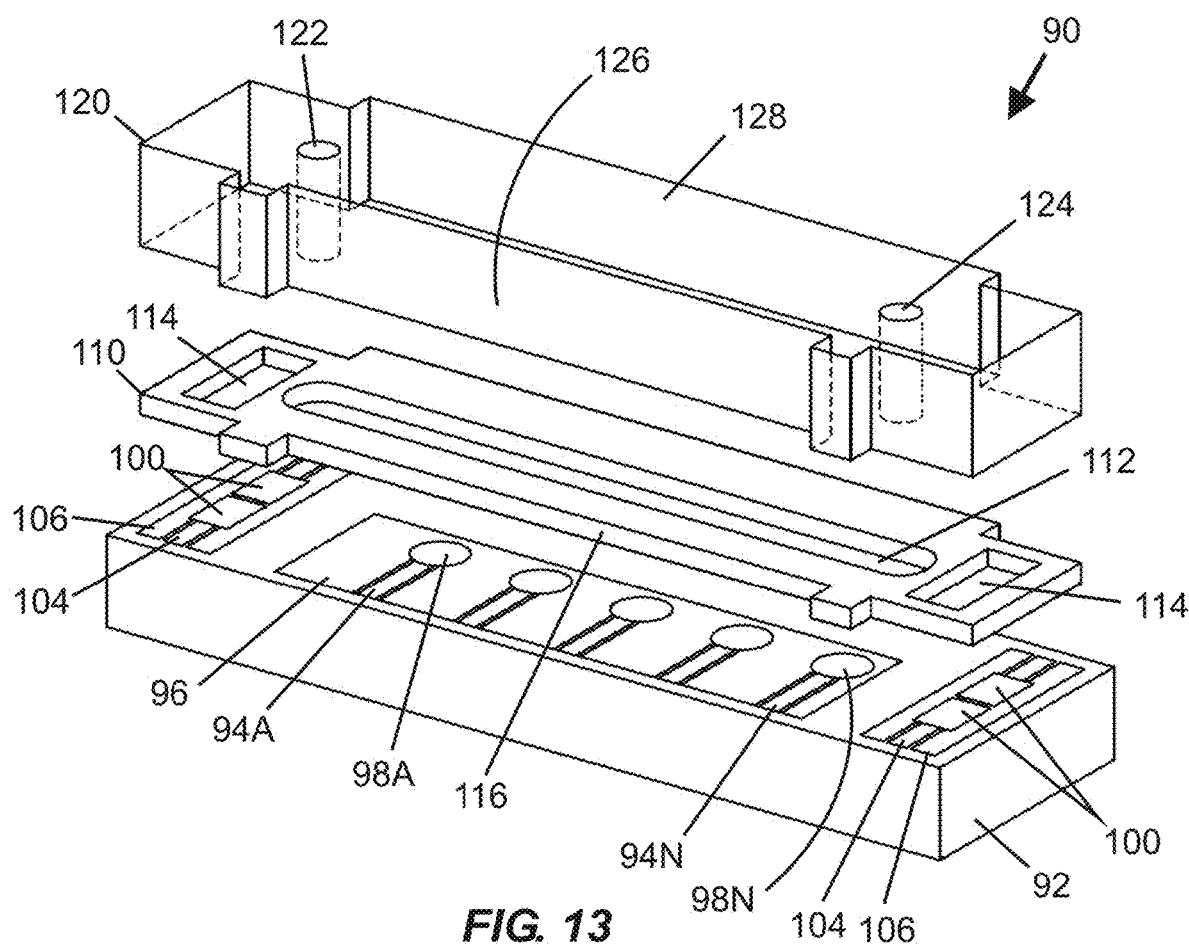
FIG. 13 is a perspective assembly view of a microfluidic device incorporating a base structure including multiple bulk acoustic wave MEMS resonator devices as disclosed herein, an intermediate wall structure layer defining lateral boundaries of a microfluidic channel containing active regions of the MEMS resonator devices, and a cover structure layer defining an upper boundary of the microfluidic channel.

FIG. 13 is a perspective assembly view of a microfluidic device 90 incorporating a substrate 92 with multiple bulk acoustic wave MEMS resonator devices (forming a base structure), an intermediate wall structure layer 110 defining a central microfluidic channel 112 registered with active regions 98A-98N of the MEMS resonator devices, and a cover structure layer 120 arranged to cover the intermediate wall structure layer 110. Top central portions of the substrate 92, which includes an acoustic reflector (not shown) and a piezoelectric material (not shown), include a top side electrode 96 and bottom side electrodes 94A-94N. Regions in which the foregoing electrodes overlap one another and sandwich the piezoelectric material embody active regions 98A-98N. Any suitable number of active regions 98A-98N may be provided and fluidically arranged in series or parallel, although five active regions are illustrated in FIG. 13. Top peripheral (or top end) portions of the substrate 92 further include reference top side electrodes 106 and reference bottom side electrodes 104 in communication with reference overlap regions 100. Such reference overlap regions 100 are not exposed to fluid, and are present to provide a basis for comparing signals obtained from the active regions 98A-98N exposed to fluid within the central microfluidic channel 112. The substrate 92 is overlaid with the intermediate wall structure layer 110, wherein the central microfluidic channel 112 is intended to receive fluid, and defines peripheral chambers 114 arranged to overlie the reference overlap regions 100 in a sealed fashion. The intermediate wall structure layer 110 may be formed of any suitable material such as SU-8 negative epoxy resist, other photoresist material, or laser-cut "stencil" layers of thin polymeric materials optionally including one or more self-adhesive surfaces (e.g., adhesive tape), etc. The intermediate wall structure layer 110 further includes a lateral inset region 116 that enables lateral portions of the top side electrode 96 and bottom side electrodes 94A-94N to be accessed upon assembly of the microfluidic device 90. The cover structure layer 120 includes a lateral inset region 126 registered with the lateral inset region 116 of the intermediate wall structure layer 110, and includes microfluidic ports 122, 124 accessible along a top surface 128 of the cover structure layer 120 and registered with end portions of the central microfluidic channel 112 defined in the intermediate wall structure layer 110 to permit fluid (e.g., liquid) to be supplied to the central microfluidic channel 112 over the active regions 98A-98N. Preferably, at least the electrodes 94A-94N, 96 are overlaid with a hermeticity layer, an interface layer, a self-assembled monolayer, and functionalization (e.g., specific binding) material as disclosed herein. In certain embodiments, a driving circuits may be configured to apply alternating current to the electrodes 94A-94N, 96 to cause the piezoelectric material to selectively exhibit a dominant shear response. Although not shown, it is to be appreciated that multiple absorbers including functionalization material may be provided on surfaces bounding the central microfluidic channel 112, including one or more of the following: the base structure (extending upward from piezoelectric material and/or electrodes formed over the substrate 92 in areas non-coincident with the active regions 98A-98N), the intermediate wall structure layer 110, or the cover structure layer 120. Microfluidic devices according to other configurations may be provided, as will be recognized by those skilled in the art upon review of the present disclosure.

Technical benefits obtainable with various embodiments of the present disclosure may include one or more of the following: enhanced dynamic measurement range of bulk acoustic wave resonator-based sensing devices (e.g., including devices suitable biosensing or biochemical sensing applications), and enablement of using undiluted samples with bulk acoustic resonator-based biosensing or biochemical sensing devices.

Those skilled in the art will recognize improvements and modifications to the preferred embodiments of the present disclosure. All such improvements and modifications are considered within the scope of the concepts disclosed herein and the claims that follow.

What is claimed is:
1. A fluidic device comprising:
 a base structure comprising: (i) a substrate; (ii) at least one bulk acoustic wave resonator structure supported by the substrate, the at least one bulk acoustic wave resonator structure including a piezoelectric material, a top side electrode arranged over a portion of the piezoelectric material, and a bottom side electrode arranged below at least a portion of the piezoelectric material, wherein a portion of the piezoelectric material is arranged between the top side electrode and the bottom side electrode to form an active region; and (iii) functionalization material arranged over at least a portion of the active region of the at least one bulk acoustic wave resonator structure to form at least one functionalized active region;
 a wall structure arranged over at least a portion of the base structure and defining lateral boundaries of a fluidic passage containing the active region and being configured to receive a fluid comprising multiple constituents; and
 a cover structure arranged over the wall structure and defining an upper boundary of the fluidic passage;
 wherein the base structure defines a lower boundary of the fluidic passage; and wherein one or more of the wall structure, the cover structure, or a portion of the base structure non-coincident with the active region comprises additional functionalization material disposed in a fixed position relative to the one or more of the wall structure, the cover structure, or a portion of the base structure non-coincident with the active region during detection of at least one analyte to form at least one absorber configured to bind the at least one analyte.

2. The fluidic device of claim 1, wherein the at least one functionalized active region comprises a first aggregate surface area exposed to the fluidic passage, and the at least one absorber comprises a second aggregate surface area exposed to the fluidic passage that is greater than the first aggregate surface area exposed to the fluidic passage.

3. The fluidic device of claim 2, wherein the second aggregate surface area exposed to the fluidic passage is at least about 10 times greater than the first aggregate surface area exposed to the fluidic passage.

4. The fluidic device of claim 1, wherein the additional functionalization material of the at least one absorber comprises a same chemical or biological composition as the functionalization material of the at least one functionalized active region.

5. The fluidic device of claim 1, wherein:
the at least one bulk acoustic wave resonator structure comprises a plurality of bulk acoustic wave resonator structures;
the at least one functionalized active region comprises a plurality of functionalized active regions;
the at least one absorber comprises a plurality of absorbers; and
at least some absorbers of the plurality of absorbers are arranged upstream of one or more functionalized active regions of the plurality of functionalized active regions, relative to a direction of flow of the fluid comprising multiple constituents through the fluidic passage.

6. The fluidic device of claim 1, further comprising a blocking material arranged over at least a portion of one or more of the wall structure, the cover structure, or the base structure at locations non-coincident with the functionalization material or the additional functionalization material.

7. The fluidic device of claim 1, wherein the wall structure and the cover structure are embodied in a monolithic body structure.

8. The fluidic device of claim 1, wherein the wall structure and the base structure are embodied in a monolithic body structure.

9. The fluidic device of claim 1, wherein the cover structure comprises a cover layer, the wall structure comprises at least one wall layer, and the at least one wall layer is arranged between the base structure and the cover layer.

10. The fluidic device of claim 1, wherein the base structure further comprises at least one acoustic reflector element arranged between the substrate and the at least one bulk acoustic wave resonator structure.

11. The fluidic device of claim 1, wherein the substrate defines a recess arranged below the active region.

12. The fluidic device of claim 1, wherein the piezoelectric material comprises a c-axis having an orientation distribution that is predominantly non-parallel to normal of a face of the substrate.

13. The fluidic device of claim 1, further comprising a self-assembled monolayer arranged between the functionalization material of the at least one functionalized active region and the top side electrode.

14. The fluidic device of claim 13, further comprising an interface layer arranged between the self-assembled monolayer and the top side electrode.

15. The fluidic device of claim 14, further comprising a hermeticity layer arranged between the interface layer and the top side electrode.

16. A method for biological or chemical sensing, the method comprising:
supplying a fluid containing an analyte into the fluidic passage of the fluidic device according to claim 1, wherein said supplying is configured to cause a first portion of the analyte to bind to the additional functionalization material of the at least one absorber and to cause a second portion of the analyte to bind to the functionalization material of the at least one functionalized active region;
inducing a bulk acoustic wave in the active region of the at least one bulk acoustic wave resonator structure; and
sensing a change in at least one of an amplitude-magnitude property, a frequency property, or a phase property of the at least one bulk acoustic wave resonator structure to indicate at least one of presence or quantity of analyte bound to the functionalization material of the at least one functionalized active region.

17. A method for fabricating a fluidic device, the method comprising:
forming a base structure including at least one bulk acoustic wave resonator structure supported by a substrate, wherein the at least one bulk acoustic wave resonator structure includes a piezoelectric material, a top side electrode arranged over a portion of the piezoelectric material, a bottom side electrode arranged below at least a portion of the piezoelectric material, and an active region formed by a portion of the piezoelectric material arranged between the top side electrode and the bottom side electrode;
forming a wall structure and a cover structure over at least a portion of the base structure, wherein: the wall structure defines lateral boundaries of a fluidic passage containing the active region and is configured to receive a fluid comprising multiple constituents, the cover structure is arranged over the wall structure and defines an upper boundary of the fluidic passage, and a lower boundary of the fluidic passage is defined by the base structure;
depositing functionalization material over the active region of the at least one bulk acoustic wave resonator structure to form at least one functionalized active region; and
depositing additional functionalization material over one or more of at least a portion of the wall structure, at least a portion of the cover structure, or a portion of the base structure non-coincident with the active region to form at least one absorber to bind at least one analyte, wherein the additional functionalization material is disposed in a fixed position relative to the one or more of the wall structure, the cover structure, or a portion of the base structure non-coincident with the active region during detection of the at least one analyte.

18. The method of claim 17, wherein at least one of (i) depositing the functionalization material over the active region of the at least one bulk acoustic wave resonator structure, or (ii) depositing the additional functionalization material over one or more of at least a portion of the wall structure, at least a portion of the cover structure, or a portion of the base structure non-coincident with the active region, is performed after forming of at least one of the wall structure or the cover structure over at least a portion of the base structure.

19. The method of claim 17, further comprising depositing a self-assembled monolayer over one or more of at least a portion of the wall structure, at least a portion of the cover structure, or a portion of the base structure non-coincident with the active region.

20. The method of claim 17, further comprising depositing a blocking material over at least a portion of one or more of the wall structure, the cover structure, or the base structure at locations non-coincident with the functionalization material and non-coincident with the additional functionalization material.

* * * * *